(12) United States Patent
Johansen et al.

(10) Patent No.: US 8,309,338 B2
(45) Date of Patent: Nov. 13, 2012

(54) POLYPEPTIDES HAVING ENDOGLUCANASE ACTIVITY AND POLYNUCLEOTIDES ENCODING SAME

(75) Inventors: Katja Salomon Johansen, Gentofte (DK); Keith Gibson, Bagsvaerd (DK); Preben Nielsen, Hoersholm (DK); Helle Outtrup, Vaerloese (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 13/093,350

(22) Filed: Apr. 25, 2011

(65) Prior Publication Data

US 2011/0201082 A1  Aug. 18, 2011

Related U.S. Application Data

(63) Continuation of application No. 12/090,400, filed as application No. PCT/EP2006/068509 on Nov. 15, 2006, now abandoned.

(60) Provisional application No. 60/738,430, filed on Nov. 21, 2005.

(30) Foreign Application Priority Data

Nov. 16, 2005 (DK) ................................ 2005 01599

(51) Int. Cl.
*C12N 9/42* (2006.01)
*C12N 9/08* (2006.01)
*C11D 3/00* (2006.01)

(52) U.S. Cl. .................... 435/209; 435/192; 510/392

(58) Field of Classification Search ........................ None
See application file for complete search history.

(56) References Cited

FOREIGN PATENT DOCUMENTS

| | | |
|---|---|---|
| EP | 0 307 564 A2 | 3/1989 |
| EP | 0 435 876 B1 | 6/1994 |
| GB | 1 368 599 | 10/1974 |
| JP | 1281090 | 11/1989 |
| JP | 07-203960 | 8/1995 |
| JP | 2000-210081 | 8/2000 |
| WO | WO 91/10732 A1 | 7/1991 |
| WO | WO 91/17243 A1 | 11/1991 |
| WO | WO 91/17244 A1 | 11/1991 |
| WO | WO 95/24471 A1 | 9/1995 |
| WO | WO 95/26398 A1 | 10/1995 |
| WO | WO 02/099091 A2 | 12/2002 |

OTHER PUBLICATIONS

Gilbert et al., Journal of General Microbiology, vol. 139, pp. 187-194 (1993).
Gilkes et al., Microbiological Reviews, vol. 55, No. 2, pp. 303-315 (1991).
Guo et al., Proceedings of the National Academy of Sciences of the USA, vol. 101, No. 25, pp. 9205-9210 (2004).
Henrissat et al., Biochem. J., vol. 293, pp. 781-788 (1993).
Henrissat et al., Biochem. J., vol. 280, pp. 309-316 (1991).
Hilden et al., Biotechnology Letters, vol. 26, No. 22, pp. 1683-1693 (2004).
KAO Corp., abstract of JP 07203960 (1995).
KAO Corp., Database Geneseq, Accession No. AAR07478 (1988).
KAO Corp., Database Geneseq, Accession No. AAR77395 (1996).
KAO Corp., Database JPO Proteins (XP-002416534) (1989).
Katsuya et al., Database JPO Proteins, Accession No. E56081 (1987).
Meinkoth et al., Current Protocols in Molecular Biology, vol. 2.10. 8-2.10.11 (1993).
Nielsen et al., Protein Expression and Purification, vol. 26, No. 1, pp. 1-8 (2002).
Ozaki et al., Journal of General Microbiology, vol. 136, No. 7, pp. 1327-1334 (1990).
Shirai et al., Database UniProt, Accession No. P19424 (1990).
Witkowski et al., Biochemistry, vol. 38, pp. 11643-11650 (1999).
Shirai et al., Journal of Biochemistry, vol. 122, pp. 638-685 (1997).

*Primary Examiner* — Tekchand Saidha
*Assistant Examiner* — Younus Meah
(74) *Attorney, Agent, or Firm* — Elias Lambiris

(57) ABSTRACT

The present invention relates to isolated polypeptides having endoglucanase activity and isolated polynucleotides encoding the polypeptides. The invention also relates to nucleic acid constructs, vectors, and host cells comprising the polynucleotides as well as methods for producing and using the polypeptides.

29 Claims, 8 Drawing Sheets

Figure 1A

```
         ---------+---------+---------+---------+---------+
                 10        20        30        40        50
         ---------+---------+---------+---------+---------+
  1 -----VRQPIGKKIIAAGMIFTLLFSLIV--------------------  ACE160
  1 MKIKQIKQSLSLLLIIT-LIMSLFVPMASANTNESKSNAFPFSDVKKTSW  KSM634
  1 MKIKQIKQSLSLLLIIT-LIMSLFVPMASANTNESKSNAFPFSDVKKTSW  KSM365
  1 MKIKQIKQSLSLLLIIT-LIMSLFVPMASANTNESKSNAFPFSDVKKTSW  KSM635
  1 ----MMLRKKTKQLISSILILVLLLSLFP--------------------  KSM64
  1 ----MMLRKKTKQLISSILILVLLLSLFP--------------------  KSM-S237
  1 --------------------------------------------------  MB1181

---------+---------+---------+---------+---------+
                 60        70        80        90       100
         ---------+---------+---------+---------+---------+
 25 ------------------------------TVFPTAGQALES---DY  ACE160
 50 SFPYIKDLYEQEVITGTSATTFSPTDSVTRAQFTVMLTRGLGLEASSKDY  KSM634
 50 SFPYIKDLYEQEVITGTSATTFSPTDSVTRAQFTVMLTRGLGLEASSKDY  KSM365
 50 SFPYIKDLYEQEVITGTSATTFSPTDSVTRAQFTVMLTRGLGLEASSKDY  KSM635
 26 ---------------------------TALAAEGNTRED---NF  KSM64
 26 ---------------------------AALAAEGNTRED---NF  KSM-S237
  1 ------------------------------AEGNTRED---NF  MB1181

---------+---------+---------+---------+---------+
                110       120       130       140       150
         ---------+---------+---------+---------+---------+
 39 SHLLGN----DAVKRPSE-----G-----------------GALS----  ACE160
100 PFKDRKNWAYKEIQAAYEAGIVTGKTNGEFAPNENITREQMAAMAVRAYE  KSM634
100 PFKDRKNWAYKEIQAAYEAGIVTGKTNGEFAPNENITREQMAAMAVRAYE  KSM365
100 PFKDRKNWAYKEIQAAYEAGIVTGKTNGEFAPNENITREQMAAMAVRAYE  KSM635
 40 KHLLGN----DNVKRPSE--------------------------------  KSM64
 40 KHLLGN----DNVKRPSE--------------------------------  KSM-S237
 11 KHLLGN----DNVKRPSE--------------------------------  MB1181
```

Figure 1B

```
         ---------+---------+---------+---------+---------+
              160       170       180       190       200
         ---------+---------+---------+---------+---------+
  58 -LCNETTP--------------------VK-----------------PNH ACE160
 150 YLENELSLPEEQREYNDSSSISTFAQDAVQKAYVLELMEGNTDGYFQPKR KSM634
 150 YLENELSLPEEQREYNDSSSISTFAQDAVQKAYVLELMEGNTDGYFQPKR KSM365
 150 YLENELSLPEEQREYNDSSSISTFAQDAVQKAYVLELMEGNTDGYFQPKR KSM635
  54 ------------------------------------------------- KSM64
  54 ------------------------------------------------- KSM-S237
  25 ------------------------------------------------- MB1181

---------+---------+---------+---------+---------+
              210       220       230       240       250
         ---------+---------+---------+---------+---------+
  70 AGDRGKP------------S-----HAGKGK-PPHAGKPEHAGPK-RKTL ACE160
 200 NSTREQSAKVISTLLWKVASHDYLYHTEAVKSPSEAGALQLVELNGQLTL KSM634
 200 NSTREQSAKVISTLLWKVASHDYLYHTEAVKSPSEAGALQLVELNGQLTL KSM365
 200 NSTREQSAKVISTLLWKVASHDYLYHTEAVKSPSEAGALQLVELNGQLTL KSM635
  54 ----------------------------------AGALQLQEVDGQMTL KSM64
  54 ----------------------------------AGALQLQEVDGQMTL KSM-S237
  25 ----------------------------------AGALQLQEVDGQMTL MB1181

---------+---------+---------+---------+---------+
              260       270       280       290       300
         ---------+---------+---------+---------+---------+
 101 CDATGSQIQLRGMSTHGLQWFGEIINDNAFAALSNDWEANMIRLAMYIGE ACE160
 250 AGEDGTPVQLRGMSTHGLQWFGEIVNENAFVALSNDWGSNMIRLAMYIGE KSM634
 250 AGEDGTPVQLRGMSTHGLQWFGEIVNENAFVALSNDWGSNMIRLAMYIGE KSM365
 250 AGEDGTPVQLRGMSTHGLQWFGEIVNENAFVALSNDWGSNMIRLAMYIGE KSM635
  69 VDQHGEKIQLRGMSTHGLQWFPEILNDNAYKALANDWESNMIRLAMYVGE KSM64
  69 VDQHGEKIQLRGMSTHGLQWFPEILNDNAYKALSNDWDSNMIRLAMYVGE KSM-S237
  40 VDQHGEKIQLRGMSTHGLQWFPEILNDNAYKALANDWESNMIRLAMYVGE MB1181
```

Figure 1C

```
        ---------+---------+---------+---------+---------+
             310       320       330       340       350
        ---------+---------+---------+---------+---------+
151 NGYATNP-EVKELVYEGIELAFKHDMYVIVDWHVHAPGDPRADIYSGALD ACE160
300 NGYATNP-EVKDLVYEGIELAFEHDMYVIVDWHVHAPGDPRADVYSGAYD KSM634
300 NGYATNP-EVKDLVYEGIELAFEHDMYVIVDWHVHAPGDPRADVYSGAYD KSM365
300 NGYATNP-EVKDLVYEGIELAFEHDMYVIVDWHVHAPGDPRADVYSGAYD KSM635
119 NGYASNPELIKSRVIKGIDLAIENDMYVIVDWHVHAPGDPRDPVYAGAED KSM64
119 NGYATNPELIKQRVIDGIELAIENDMYVIVDWHVHAPGDPRDPVYAGAKD KSM-S237
 90 NGYASNPELIKSRVIKGIDLAIENDMYVIVDWHVHAPGDPRDPVYAGAED MB1181

---------+---------+---------+---------+---------+
             360       370       380       390       400
        ---------+---------+---------+---------+---------+
200 FFKEIADHYKDHPKFHYIIWEIANEPSPNNSGGPGIPNDETGWKAVKEYA ACE160
349 FFEEIADHYKDHPKNHYIIWELANEPSPNNNGGPGLTNDEKGWEAVKEYA KSM634
349 FFEEIADHYKDHPKNHYIIWELANEPSPNNNGGPGLTNDEKGWEAVKEYA KSM365
349 FFEEIADHYKDHPKNHYIIWELANEPSPNNNGGPGLTNDEKGWEAVKEYA KSM635
169 FFRDIAALYPNNP---HIIYELANEPSSNNNGGAGIPNNEEGWNAVKEYA KSM64
169 FFREIAALYPNNP---HIIYELANEPSSNNNGGAGIPNNEEGWKAVKEYA KSM-S237
140 FFRDIAALYPNNP---HIIYELANEPSSNNNGGAGIPNNEEGWNAVKEYA MB1181

---------+---------+---------+---------+---------+
             410       420       430       440       450
        ---------+---------+---------+---------+---------+
250 EPIVEMLRERG---DNIILVGSPNWSQRPDLAADNPIDAKNIMYSVHFYT ACE160
399 EPIVEMLREKG---DNMILVGNPNWSQRPDLSADNPIDAENIMYSVHFYT KSM634
399 EPIVEMLREKG---DNMILVGNPNWSQRPDLSADNPIDAENIMYSVHFYT KSM365
399 EPIVEMLREKG---DNMILVGNPNWSQRPDLSADNPIDAENIMYSVHFYT KSM635
216 DPIVEMLRDSGNADDNIIIVGSPNWSQRPDLAADNPIDDHHTMYTVHFYT KSM64
216 DPIVEMLRKSGNADDNIIIVGSPNWSQRPDLAADNPIDDHHTMYTVHFYT KSM-S237
187 DPIVEMLRDSGNADDNIIIVGSPNWSQRPDLAADNPINDHHTMYTVHFYT MB1181
```

Figure 1D

```
        ---------+---------+---------+---------+---------+
              460       470       480       490       500
        ---------+---------+---------+---------+---------+
297  GSHEPSDTSYPEGTPSSERNNVMANVRYALENGAAVFATEWGTSQANGDG  ACE160
446  GSHGASHIGYPEGTPSSERSNVMANVVLLLDNGVAVFATEWGTSQANGDG  KSM634
446  GSHGASHIGYPEGTPSSERSNVMANVRYALDNGVAVFATEWGTSQANGDG  KSM365
446  GSHGASHIGYPEGTPSSERSNVMANVRYALDNGVAVFATEWGTSQANGDG  KSM635
266  GSHAASTESYPPETPNSERGNVMSNTRYALENGVAVFATEWGTSQANGDG  KSM64
266  GSHAASTESYPSETPNSERGNVMSNTRYALENGVAVFATEWGTSQASGDG  KSM-S237
237  GSHAASTESYPPETPNSERGNVMSNTRYALENGVAVFATEWGTSQANGDG  MB1181

---------+---------+---------+---------+---------+
              510       520       530       540       550
        ---------+---------+---------+---------+---------+
347  GPYLDEADVWLNFLNENNISWVNWSLTNKNETSGSFTPFELGKSNATSLD  ACE160
496  GPYFDEADVWLNFLNKHNISWANWSLTNKNEISGAFTPFELGRTDATDLD  KSM634
496  GPYFDEADVWLNFLNKHNISWANWSLTNKNEISGAFTPFELGRTDATDLD  KSM365
496  GPYFDEADVWLNFLNKHNISWANWSLTNKNEISGAFTPFELGRTDATDLD  KSM635
316  GPYFDEADVWIEFLNENNISWANWSLTNKNEVSGAFTPFELGKSNATSLD  KSM64
316  GPYFDEADVWIEFLNENNISWANWSLTNKNEVSGAFTPFELGKSNATNLD  KSM-S237
287  GPYFDEADVWIEFLNENNISWANWSLTNKNEVSGAFTPFELGKSNATNLD  MB1181

---------+---------+---------+---------+---------+
              560       570       580       590       600
        ---------+---------+---------+---------+---------+
397  PGPEQAWSLPELSVSGEYVRSRIKGSPYEPFDRTKFNKVIWDFNDGTVQG  ACE160
546  PGANQVWAPEELSLSGEYVRARIKGIEYTPIDRTKFTKLVWDFNDGTTQG  KSM634
546  PGANQVWAPEELSLSGEYVRARIKGIEYTPIDRTKFTKLVWDFNDGTTQG  KSM365
546  PGANQVWAPEELSLSGEYVRARIKGIEYTPIDRTKFTKLVWDFNDGTTQG  KSM635
366  PGPDQVWVPEELSLSGEYVRARIKGVNYEPIDRTKYTKVLWDFNDGTKQG  KSM64
366  PGPDHVWAPEELSLSGEYVRARIKGVNYEPIDRTKYTKVLWDFNDGTKQG  KSM-S237
337  PGPDHVWAPEELSLSGEYVRARIKGVNYEPIDRTKYTKVLWDFNDGTKQG  MB1181
```

Figure 1E

```
         ---------+---------+---------+---------+---------+
                610       620       630       640       650
         ---------+---------+---------+---------+---------+
447 FEVNDDSPVKEEIAVSNAGNALQITGLNASNDISTDNFWSNLRLSANSWG ACE160
596 FQVNGDSPNKESITLSNNNDALQIEGLNVSNDISEGNYWDNVRLSADGWS KSM634
596 FQVNGDSPNKESITLSNNNDALQIEGLNVSNDISEGNYWDNVRLSADGWS KSM365
596 FQVNGDSPNKESITLSNNNDALQIEGLNVSNDISEGNYWDNVRLSADGWS KSM635
416 FGVNGDSP-VEDVVIENEAGALKLSGLDASNDVSEGNYWANARLSADGWG KSM64
416 FGVNSDSPNKELIAVDNENNTLKVSGLDVSNDVSDGNFWANARLSANGWG KSM-S237
387 FGVNSDSPNKELIAVDNENNTLKVSGLDVSNDVSDGNFWANARLSADGWG MB1181

---------+---------+---------+---------+---------+
                660       670       680       690       700
         ---------+---------+---------+---------+---------+
497 ESVNILGAEELTLDVIVDEPTSVSIAAIPQSAAVGWANPNNAVVVSKEDF ACE160
646 ENVDILGATELTIDVIVEEPTTVSIAAIPQGPAAGWANPTRAIKVTEDDF KSM634
646 ENVDILGATELTIDVIVEEPTTVSIAAIPQGPAAGWANPTRAIKVTEDDF KSM365
646 ENVDILGATELTIDVIVEEPTTVSIAAIPQGPAAGWANPTRAIKVTEDDF KSM635
465 KSVDILGAEKLTMDVIVDEPTTVSIAAIPQGPSANWVNPNRAIKVEPTNF KSM64
466 KSVDILGAEKLTMDVIVDEPTTVAIAAIPQSSKSGWANPERAVRVNAEDF KSM-S237
437 KSVDILGAEKLTMDVIVDEPTTVAIAAIPQSSKSGWANPERAVRVNAEDF MB1181

---------+---------+---------+---------+---------+
                710       720       730       740       750
         ---------+---------+---------+---------+---------+
547 APYGG-QYKAVLTITPEDSPALGAIATHSDDNMMNNIILFIGTENADVLS ACE160
696 ESFGD-GYKALVTITSEDSPSLETIATSPEDNTMSNIILFVGTEDADVIS KSM634
696 ESFGD-GYKALVTITSEDSPSLETIATSPEDNTMSNIILFVGTEDADVIS KSM365
696 ESFGD-GYKALVTITSEDSPSLETIATSPEDNTMSNIILFVGTEDADVIS KSM635
515 VPLGD-KFKAELTITSADSPSLEAIAMHAENNNINNIILFVGTEGADVIY KSM64
516 VQQTDGKYKAGLTITGEDAPNLKNIAFHEEDNNMNNIILFVGTDAADVIY KSM-S237
487 VQQTDGKYKAGLTITGEDAPNLKNIAFHEEDNNMNNIILFVGTDAADVIY MB1181
```

Figure 1F

```
    ---------+---------+---------+---------+---------+
           760       770       780       790       800
    ---------+---------+---------+---------+---------+
596 LDNITVKGSIVEIPVIHDPKGIAVLPSNFEDGTRQGWDWNPESGVKTALT  ACE160
745 LDNITVSGTEIEIEVIHDEKGTATLPSTFEDGTRQGWDWHTESGVKTALT  KSM634
745 LDNITVSGTEIEIEVIHDEKGTATLPSTFEDGTRQGWDWHTESGVKTALT  KSM365
745 LDNITVSGTEIEIEVIHDEKGTATLPSTFEDGTRQGWDWHTESGVKTALT  KSM635
564 LDNIKVIGTEVEIPVVHDPKGEAVLPSVFEDGTRQGWDWAGESGVKTALT  KSM64
566 LDNIKVIGTEVEIPVVHDPKGEAVLPSVFEDGTRQGWDWAGESGVKTALT  KSM-S237
537 LDNIKVIGTEVEIPVVHDPKGEAVLPSVFEDGTRQGWDWAGESGVKTALT  MB1181

---------+---------+---------+---------+---------+
           810       820       830       840       850
    ---------+---------+---------+---------+---------+
646 IKEADGSHALSWEFAYPEVKPGDGWATAPRLEFWKDGLVRGANDYLSFDL  ACE160
795 IEEANGSNALSWEYAYPEVKPSDGWATAPRLDFWKDELVRGTSDYISFDF  KSM634
795 IEEANGSNALSWEYAYPEVKPSDGWATAPRLDFWKDELVRGTSDYISFDF  KSM365
795 IEEANGSNALSWEYAYPEVKPSDGWATAPRLDFWKDELVRGTSDYISFDF  KSM635
614 IEEANGSNALSWEFGYPEVKPSDNWATAPRLDFWKSDLVRGENDYVTFDF  KSM64
616 IEEANGSNALSWEFGYPEVKPSDNWATAPRLDFWKSDLVRGENDYVAFDF  KSM-S237
587 IEEANGSNALSWEFGYPEVKPSDNWATAPRLDFWKSDLVRGENDYVAFDF  MB1181

---------+---------+---------+---------+---------+
           860       870       880       890       900
    ---------+---------+---------+---------+---------+
696 YLDPVRATEGAITTHLVFQPPSAGYWVQAPASHSIDLLNLDSADITADGL  ACE160
845 YIDAVRASEGAISINAVFQPPANGYWQEVPTTFEIDLTELDSATVTSDEL  KSM634
845 YIDAVRASEGAISINAVFQPPANGYWQEVPTTFEIDLTELDSATVTSDEL  KSM365
845 YIDAVRASEGAISINAVFQPPANGYWQEVPTTFEIDLTELDSATVTSDEL  KSM635
664 YLDPVRATEGAMNINLVFQPPTNGYWVQAPKTYTINFDELEEAN-QVNGL  KSM64
666 YLDPVRATEGAMNINLVFQPPTNGYWVQAPKTYTINFDELEEAN-QVNGL  KSM-S237
637 YLDPVRATEGAMNINLVFQPPTNGYWVQAPKTYTINFDELEEAN-QVNGL  MB1181
```

Figure 1G

```
        ---------+---------+---------+---------+---------+
               910       920       930       940       950
        ---------+---------+---------+---------+---------+
746  YHYEVKFNIRDITAIQDDTALRNMILILEDRNSDFAGRAFIDNVRFE.      ACE160
895  YHYEVKINIRDIEAITDDTELRNLLLIFADEDSDFAGRVFVDNVRFE       KSM634
895  YHYEVKINIRDIEAITDDTELRNLLLIFADEDSDFAGRVFVDNVRFE       KSM365
895  YHYEVKINIRDIEAITDDTELRNLLLIFADEDSDFAGRVFVDNVRFE       KSM635
713  YHYEVKINVRDITNIQDDTLLRNMMIIFADVESDFAGRVFVDNVRFEGAA    KSM64
715  YHYEVKINVRDITNIQDDTLLRNMMIIFADVESDFAGRVFVDNVRFEGAA    KSM-S237
686  YHYEVKINVRDITNIQDDTLLRNMMIIFADVESDFAGRVFVDNVRFEGAA    MB1181

---------+---------+---------+---------+---------+
               960       970       980       990      1000
        ---------+---------+---------+---------+---------+
793                                                         ACE160
941                                                         KSM634
941                                                         KSM365
941                                                         KSM635
763  TTEPVEPEPVDPGEETPPVDEKEAKKEQKEAEKEEKEAVKEEKKEAKEEK   KSM64
765  TTEPVEPEPVDPGEETPPVDEKEAKKEQKEAEKEEKEAVKEEKKEAKEEK   KSM-S237
736  TTEPVEPEPVDPGEETPPVDEKEAKKEQKEAEKEEKEE               MB1181

---------+
              1010
        ---------+
793                                                         ACE160
941                                                         KSM634
941                                                         KSM365
941                                                         KSM635
813  KAIKNEATKK                                             KSM64
815  KAVKNEAKKK                                             KSM-S237
773                                                         MB1181
```

POLYPEPTIDES HAVING ENDOGLUCANASE ACTIVITY AND POLYNUCLEOTIDES ENCODING SAME

CROSS-REFERENCE TO RELATED APPLICATIONS

This application is a continuation of U.S. application Ser. No. 12/090,400 filed on Apr. 16, 2008, now abandoned, which is a 35 U.S.C. 371 national application of PCT/EP2006/068509 filed Nov. 15, 2006, which claims priority or the benefit under 35 U.S.C. 119 of Danish application no. PA 2005 01599 filed Nov. 16, 2005 and U.S. provisional application No. 60/738,430 filed Nov. 21, 2005, the contents of which are fully incorporated herein by reference.

REFERENCE TO A SEQUENCE LISTING

This application contains a Sequence Listing in computer readable form, which is incorporated herein by reference.

FIELD OF THE INVENTION

The present invention relates to isolated polypeptides having endoglucanase activity and isolated polynucleotides encoding the polypeptides. The invention also relates to nucleic acid constructs, vectors, and host cells comprising the polynucleotides as well as methods for producing and using the polypeptides in the detergent, paper and pulp, oil drilling, oil extraction, wine and juice, food ingredients, animal feed or textile industries.

BACKGROUND OF THE INVENTION

Cellulose is a polymer of glucose linked by beta-1,4-glucosidic bonds. Cellulose chains form numerous intra- and intermolecular hydrogen bonds, which result in the formation of insoluble cellulose micro-fibrils. Microbial hydrolysis of cellulose to glucose involves the following three major classes of cellulases: (i) endoglucanases (EC 3.2.1.4) which cleave beta-1,4-glucosidic links randomly throughout cellulose molecules, also called endo-beta-1,4-glucanases; (ii) cellobiohydrolases (EC 3.2.1.91) which digest cellulose from the non-reducing end, releasing cellobiose; and (iii) beta-glucosidases (EC 3.2.1.21) which hydrolyse cellobiose and low molecular-weight cellodextrins to release glucose.

Beta-1,4-glucosidic bonds are also present in other naturally occurring polymers, e.g., in the beta-glucans from plants such as barley and oats. In some cases, endoglucanases also provide hydrolysis of such non-cellulose polymers.

Cellulases are produced by many microorganisms and are often present in multiple forms. Recognition of the economic significance of the enzymatic degradation of cellulose has promoted an extensive search for microbial cellulases, which can be used industrially. As a result, the enzymatic properties and the primary structures of a large number of cellulases have been investigated. On the basis of the results of a hydrophobic cluster analysis of the amino acid sequence of the catalytic domain, these cellulases have been placed into different families of glycosyl hydrolases; fungal and bacterial glycosyl hydrolases have been grouped into 35 families (Henrissat, "A classification of glycosyl hydrolases based on amino acid sequence similarities", Biochem. J. 280: 309-316 (1991); Henrissat and Bairoch, "New families in the classification of glycosyl hydrolases based on amino acid sequence similarities", Biochem. J. 293: 781-788 (1993)). Most cellulases consist of a carbohydrate binding module (CBM) and a catalytic domain (CAD) separated by a linker which may be rich in proline and hydroxy amino acid residues. Another classification of cellulases has been established on the basis of the similarity of their CBMs (Gilkes et al. (1991)) giving five families of glycosyl hydrolases (I-V).

Cellulases are synthesized by a large number of microorganisms which include fungi, actinomycetes, myxobacteria and true bacteria but also by plants. Especially endo-beta-1,4-glucanases of a wide variety of specificities have been identified. Many bacterial endoglucanases have been described (Gilbert and Hazlewood, 1993, J. Gen. Microbiol. 139:187-194; Henrissat and Bairoch, "New families in the classification of glycosyl hydrolases based on amino acid sequence similarities", Biochem. J. 293: 781-788 (1993)).

An important industrial use of cellulolytic enzymes is for treatment of paper pulp, e.g., for improving the drainage or for de-inking of recycled paper. Another important industrial use of cellulolytic enzymes is for treatment of cellulosic textile or fabrics, e.g., as ingredients in detergent compositions or fabric softener compositions, for bio-polishing of new fabric (garment finishing), and for obtaining a "stone-washed" look of cellulose-containing fabric, especially denim, and several methods for such treatment have been suggested, e.g., in GB 1368599, EP 0307564 and EP 0435876, WO 91/17243, WO 91/10732, WO 91/17244, WO 95/24471 and WO 95/26398. JP patent application no. 13049/1999 discloses a heat resistant alkaline cellulase derived from Bacillus sp. KSM-S237 (deposited as FERM-P-16067) suitable for detergents.

There is an ever existing need for providing novel cellulase enzymes or enzyme preparations which may be used for applications where cellulase, preferably an endo-beta-1,4-glucanase, activity (endoglucanase, EC 3.2.1.4) is desirable.

The object of the present invention is to provide polypeptides and polypeptide compositions having substantial beta-1,4-glucanase activity under slightly acid to alkaline conditions and improved performance in paper pulp processing, textile treatment, laundry processes, extraction processes or in animal feed; preferably such novel well-performing endoglucanases are producible or produced by using recombinant techniques in high yields.

SUMMARY OF THE INVENTION

The present invention relates to isolated polypeptides having endoglucanase activity selected from the group consisting of:

(a) a polypeptide having an amino acid sequence which has at least 72% identity with amino acids 1 to 759 of SEQ ID NO: 2;

(b) a polypeptide which is encoded by a nucleotide sequence which hybridizes under at least low stringency conditions with (i) nucleotides 100 to 2376 of SEQ ID NO: 1, or (ii) a complementary strand of (i); and (c) a variant comprising a conservative substitution, deletion, and/or insertion of one or more amino acids of amino acids 1 to 759 of SEQ ID NO: 2.

The present invention also relates to isolated polynucleotides encoding polypeptides having endoglucanase activity, selected from the group consisting of:

(a) a polynucleotide encoding a polypeptide having an amino acid sequence which has at least 72% identity with amino acids 1 to 759 of SEQ ID NO: 2;

(b) a polynucleotide which hybridizes under at least low stringency conditions with (i) nucleotides 100 to 2376 of SEQ ID NO: 1, or (ii) a complementary strand of (i).

The present invention also relates to nucleic acid constructs, recombinant expression vectors, and recombinant host cells comprising the polynucleotides.

The present invention also relates to methods for producing such polypeptides having endoglucanase activity comprising (a) cultivating a recombinant host cell comprising a nucleic acid construct comprising a polynucleotide encoding the polypeptide under conditions conducive for production of the polypeptide; and (b) recovering the polypeptide.

The endo-beta-1,4-glucanase of the invention has stability and activity properties that make it exceptionally well-suited for use in applications involving aqueous alkaline solutions that contain surfactants and/or oxidative active species such as chemical bleaches. Such application conditions are very commonly found, both within household and industrial detergents, textile finishing treatments and in the manufacture or recycling of cellulosic pulps.

Because the endoglucanase of the invention maintains its activity to an exceptional extent under such relevant application conditions it is contemplated that it will be more useful than other known enzymes, e.g., when used in detergents, for paper/pulp processing or for textile treatments. The present invention thus also relates to methods of using the polypeptides of the invention in a detergent or textile treatment composition, a composition for treatment of paper pulp or for degradation of biomass, e.g., for the production of ethanol. Further, the invention relates to methods for washing textile, kitchenware or hard surfaces with a detergent comprising the polypeptides, methods for treatment of cellulosic textile or fabrics, such as softening, bio-polishing or stone-washing. Also, methods for improving the drainage or for de-inking of recycled paper are included.

The present invention further relates to nucleic acid constructs comprising a gene encoding a protein, wherein the gene is operably linked to one or both of a first nucleotide sequence encoding a signal peptide consisting of nucleotides 1 to 99 of SEQ ID NO: 1.

BRIEF DESCRIPTION OF THE FIGURES

FIG. 1, Alignment of the amino acid sequence of the polypeptide of the invention (ACE160, SEQ ID NO:2) with related polypeptides of the prior art. The prior art polypeptides are disclosed as:

Figure 2:
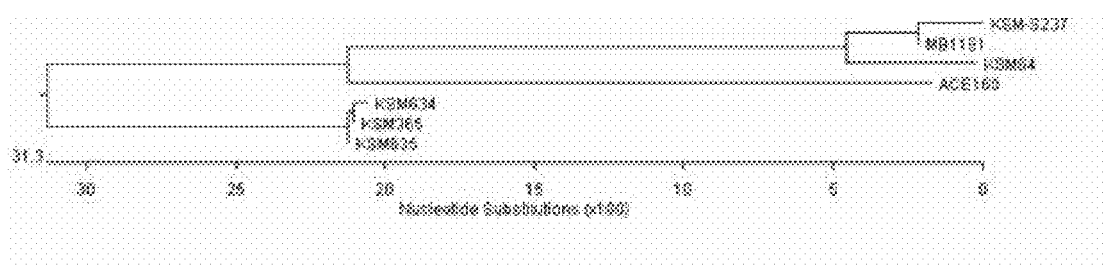

| Name | Entry number | Patent number |
| --- | --- | --- |
| KSM-64 (SEQ ID NO: 5) | ADP87708, GeneseqP | JP2004173598 |
| KSM-365 (SEQ ID NO: 6) | AAR77395, GeneseqP | JP07203960-1994 |
| KSM-634 (SEQ ID NO: 7) | AAR07478, GeneseqP | JP01281090 |
| KSM-S237 (SEQ ID NO: 8) | ADP87707, GeneseqP | JP2004173598 |
| MB1181 (SEQ ID NO: 9) | ABG76403, GeneseqP | WO200299091 |
| KSM-635 (SEQ ID NO: 10) | P19424, Uniprot | — |

FIG. 2, Phylogenetic tree showing the relationship of the endoglucanase of the invention (ACE160, SEQ ID NO:2) with prior art polypeptide sequences were constructed upon alignment with default settings in the ClustalV function of program MegAlign™ version 5.05 in DNAStar™ program package.

DEFINITIONS

Endoglucanase activity: The term "endoglucanase activity" is defined herein as a hydrolytic activity which catalyzes the endohydrolysis of 1,4-beta-D-glucosidic linkages in cellulose, lichenin and cereal beta-D-glucans, EC 3.2.1.4. A method for determination of endoglucanase activity is described below.

The polypeptides of the present invention have at least 70%, more preferably at least 80%, even more preferably at least 90%, even more preferably at least 95%, most preferably at least 98%, and even most preferably at least 100% of the endoglucanase activity of the polypeptide consisting of the amino acid sequence shown as amino acids 1 to 759 of SEQ ID NO: 2, or the catalytic core domain consisting of the amino acid 65 to 347 of SEQ ID NO: 2.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Identity: The relatedness between two amino acid sequences is described by the parameter "identity".

For purposes of the present invention, the alignment of two amino acid sequences is determined by using the Needle program from the EMBOSS package, version 2.8.0. The Needle program implements the global alignment algorithm described in Needleman and Wunsch, 1970, *J. Mol. Biol.* 48: 443-453. The substitution matrix used is BLOSUM62, gap opening penalty is 10, and gap extension penalty is 0.5.

The degree of identity between an amino acid sequence of the present invention ("invention sequence"; e.g., amino acids 1 to 759 of SEQ ID NO:2 or the catalytic core domain of amino acids 65 to 347 of SEQ ID NO:2) and a different amino acid sequence ("foreign sequence") is calculated as the number of exact matches in an alignment of the two sequences, divided by the length of the "invention sequence" or the length of the "foreign sequence", whichever is the shortest. The result is expressed in percent identity.

An exact match occurs when the "invention sequence" and the "foreign sequence" have identical amino acid residues in the same positions of the overlap (in the alignment example below this is represented by "|"). The length of a sequence is the number of amino acid residues in the sequence (e.g., the length of the "invention sequence" of SEQ ID NO:2 is 759 amino acids).

In the alignment example below, the overlap is the amino acid sequence "HTWGER.NLG" of Sequence 1; or the amino acid sequence "HGWGEDANLA" of Sequence 2. A gap is indicated by a ".".

Alignment Example

```
Sequence 1: ACMSHTWGER.NLG
                | ||| ||:
Sequence 2:     HGWGEDANLAMNPS
```

The length of the overlap of the "invention sequence" may be at least 20% of the length of the "invention sequence", more preferably at least 30%, 40%, 50%, 60%, 70%, 80%, or at least 90% of the length of the "invention sequence".

The length of the overlap of the "foreign sequence" may be at least 20% of the length of the "foreign sequence", more preferably at least 30%, 40%, 50%, 60%, 70%, 80%, or at least 90% of the length of the "invention sequence".

Polypeptide Fragment: The term "polypeptide fragment" is defined herein as a polypeptide having one or more amino acids deleted from the amino and/or carboxyl terminus of SEQ ID NO: 2 or a homologous sequence thereof, wherein the fragment has endoglucanase activity. Preferably, the fragment contains at least 283 amino acid residues, e.g., amino acids 65 to 347 of SEQ ID NO: 2.

Subsequence: The term "subsequence" is defined herein as a nucleotide sequence having one or more nucleotides deleted from the 5' and/or 3' end of SEQ ID NO: 1 or a homologous sequence thereof, wherein the subsequence encodes a polypeptide fragment having endoglucanase activity. Preferably, a subsequence contains at least 849 nucleotides, e.g., nucleic acids 193 to 1041 of SEQ ID NO:1.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99% pure, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may be a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct comprising a polynucleotide of the present invention.

DETAILED DESCRIPTION OF THE INVENTION

Polypeptides Having Endoglucanase Activity

In a first aspect, the present invention relates to isolated polypeptides having an amino acid sequence which has a degree of identity to amino acids 1 to 759 of SEQ ID NO:2, i.e., the mature polypeptide of at least 72%, more preferably at least 75%, more preferably at least 80%, more preferably at least 85%, even more preferably at least 90%, most preferably at least 95%, and even most preferably at least 97%, which have endoglucanase activity (hereinafter "homologous polypeptides"). In a preferred aspect, the homologous polypeptides have an amino acid sequence which differs by ten amino acids, preferably by five amino acids, more preferably by four amino acids, even more preferably by three amino acids, most preferably by two amino acids, and even most preferably by one amino acid from amino acids 1 to 759 of SEQ ID NO:2.

A polypeptide of the present invention preferably comprises the amino acid sequence of SEQ ID NO:2 or an allelic variant thereof; or a fragment thereof that has endoglucanase activity. In a preferred aspect, a polypeptide comprises the amino acid sequence of SEQ ID NO:2. In another preferred aspect, a polypeptide consists of the amino acid sequence of SEQ ID NO:2 or an allelic variant thereof; or a fragment thereof that has endoglucanase activity. In another preferred aspect, a polypeptide consists of the amino acid sequence of SEQ ID NO:2.

In another preferred aspect, a polypeptide comprises a catalytic core domain in amino acids 65 to 347 of SEQ ID NO:2, or an allelic variant thereof; or a fragment thereof that has endoglucanase activity. The polypeptide of the catalytic core domain has an amino acid sequence which has a degree of identity to amino acids 65 to 347 of SEQ ID NO:2 of at least 86%, more preferably at least 88%, even more preferably at least 90%, most preferably at least 95%, and even most preferably at least 97%. In another preferred aspect, a polypeptide comprises a catalytic core domain in amino acids 65 to 347 of SEQ ID NO:2, or an allelic variant thereof; or a fragment thereof that has endoglucanase activity. In another preferred aspect, a polypeptide consists of amino acids 65 to 347 of SEQ ID NO:2.

The annotation of the catalytic core domain is based on homology to cellulases of the Glycosyl hydrolase Family 5 (Henrissat, "A classification of glycosyl hydrolases based on amino acid sequence similarities", *Biochem. J.* 280: 309-316 (1991); Henrissat and Bairoch, "New families in the classification of glycosyl hydrolases based on amino acid sequence similarities", *Biochem. J.* 293: 781-788 (1993); Henrissat and Bairoch, "Updating the sequence-based classification of glycosyl hydrolases", *Biochem. J.* 316: 695-696 (1996); Davies and Henrissat, "Structures and mechanisms of glycosyl hydrolases", *Structure* 3: 853-859 (1995); Henrissat et al., "Cellulase families revealed by hydrophobic cluster analysis", *Gene* 81:83-95 (1989); Py et al., "Cellulase EGZ of *Erwinia chrysanthemi*: structural organization and importance of His98 and Glu133 residues for catalysis", *Protein Eng.* 4: 325-333 (1991)). The domain annotation of the catalytic core domain is available through afmb.cnrs-mrs.fr/CAZY/, ebi.ac.uk/interpro/, sanger.ac.uk/Software/Pfam/, or expasy.org/prosite/.

In another aspect of the invention, the polypeptide comprises a carbohydrate binding module in amino acids 368 to 569 of SEQ ID NO:2. In another preferred aspect the present invention relates to polypeptides comprising a carbohydrate binding module having a degree of identity to amino acids 368 to 569 of SEQ ID NO:2 of at least 67%, more preferably at least 70%, more preferably at least 75%, more preferably at least 80%, more preferably at least 85%, even more preferably at least 90%, most preferably at least 95%, and even most preferably at least 97%. In another preferred aspect, a polypeptide comprises a carbohydrate binding module in amino acids 368 to 569 of SEQ ID NO:2, or an allelic variant thereof; or a fragment thereof that has carbohydrate binding activity. In another preferred aspect, a polypeptide consists of amino acids 368 to 569 of SEQ ID NO:2.

The carbohydrate binding module belongs to the family 17/28. The annotation of the CBM is based on homology with known sequences, especially the CBM of KSM-635 (Ozaki et al., "Molecular cloning and nucleotide sequence of a gene for alkaline cellulase from *Bacillus* sp. KSM-635", *J. Gen. Microbiol.* 136:1327-1334 (1990), Uniprot No. P19424), which was annotated as a CBM based on relation to the galactose binding like domains described in Ito et al., "Novel thioether bond revealed by a 1.7 A crystal structure of galactose oxidase", *Nature* 350: 87-90 (1991); Macedo-Ribeiro et al., "Crystal structures of the membrane-binding C2 domain of human coagulation factor V", *Nature* 402: 434-439 (1999); Himanen et al., "Crystal structure of an Eph receptor-ephrin complex", *Nature* 414: 933-938 (2001) [PUBMED: 11780069] [PUB00010665]; and Marintchev et al., "Solution structure of the single-strand break repair protein XRCC1 N-terminal domain", *Nat. Struct. Biol.* 6: 884-893 (1999)). The domain annotation of the carbohydrate binding module is available through afmb.cnrs-mrs.fr/CAZY/, ebi.ac.uk/interpro/, sanger.ac.uk/Software/Pfam/, or expasy.org/prosite/.

In a second aspect, the present invention relates to isolated polypeptides having endoglucanase activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 100 to 2376 of SEQ ID NO: 1, (ii) a subsequence of (i) or (iii) a complementary strand of (i) or (ii) (Sambrook et al., 1989, *Molecular Cloning, A Laboratory Manual*, 2d edition, Cold Spring Harbor, N.Y.). A subsequence of SEQ ID NO: 1 contains at least 100 contiguous nucleotides or preferably at least 200 contiguous nucleotides, more preferably 300, 400, 500, 600, 700, 800, 900 contiguous nucleotides or even more preferably at least 1000 contiguous nucleotides. Moreover, the subsequence may encode a polypeptide fragment which has endoglucanase activity.

The nucleotide sequence of SEQ ID NO: 1 or a subsequence thereof, as well as the amino acid sequence of SEQ ID NO: 2 or a fragment thereof, may be used to design a nucleic acid probe to identify and clone DNA encoding polypeptides having endoglucanase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA library prepared from such other organisms may, therefore, be screened for DNA which hybridizes with the probes described above and which encodes a polypeptide having endoglucanase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1 or a subsequence thereof, the carrier material is used in a Southern blot.

For purposes of the present invention, hybridization indicates that the nucleotide sequence hybridizes to a labeled nucleic acid probe corresponding to the nucleotide sequence shown in SEQ ID NO:1, its complementary strand, or a subsequence thereof, under very low to very high stringency conditions. Molecules to which the nucleic acid probe hybridizes under these conditions can be detected using X-ray film.

In a preferred aspect, the nucleic acid probe is nucleotides 193 to 1041 of SEQ ID NO:1. In another preferred aspect, the nucleic acid probe is a polynucleotide sequence which encodes the polypeptide of SEQ ID NO:2, or a subsequence thereof. In another preferred aspect, the nucleic acid probe is SEQ ID NO:1. In another preferred aspect, the nucleic acid probe is the mature polypeptide coding region of SEQ ID NO:1.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency). Preferably, the wash is conducted using 0.2× SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides having endoglucanase activity encoded by a polynucleotide comprising nucleotides 193 to 1041 of SEQ ID NO: 1, as a unique motif.

In a fourth aspect, the present invention relates to isolated polypeptides having the following physicochemical properties: pI of 4.4, pH optimum of 9, temperature optimum of 40° C. and stability at pH from 5 to 10.5. The beta-1,4-glucanase of the invention is not significantly inactivated by Fe(II) ions. A sensitivity of the enzymatic activity of the polypeptide to the presence of ferrous ions could place restrictions on the applicability of the polypeptide, such as in processes taking place in metal containers or equipment.

In a fifth aspect, the present invention relates to artificial variants comprising a conservative substitution, deletion, and/or insertion of one or more amino acids of SEQ ID NO: 2 or the mature polypeptide thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., endoglucanase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309:59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30:10832-10837; U.S. Pat. No. 5,223,409; WO 92/06204), and region-directed mutagenesis (Derbyshire et al., 1986, *Gene* 46:145; Ner et al., 1988, *DNA* 7:127).

Sources of Polypeptides Having Endoglucanase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention may be a bacterial polypeptide. For example, the polypeptide may be a gram positive bacterial polypeptide such as a *Bacillus* polypeptide, e.g., a *Bacillus alkalophilus*, *Bacillus amyloliquefaciens*, *Bacillus brevis*, *Bacillus circulans*, *Bacillus coagulans*, *Bacillus lautus*, *Bacillus lentus*, *Bacillus licheniformis*, *Bacillus megaterium*, *Bacillus stearothermophilus*, *Bacillus subtilis*, or *Bacillus thuringiensis* polypeptide; or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

In another preferred aspect, the polypeptide is a *Bacillus* sp. ACE160 polypeptide e.g., the polypeptide of SEQ ID NO:2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of another microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to isolated polynucleotides having a nucleotide sequence which encode a polypeptide of the present invention. In a preferred aspect, the nucleotide sequence is set forth in SEQ ID NO:1. In another preferred aspect, the nucleotide sequence is the mature polypeptide coding region of SEQ ID NO:1. The present invention also encompasses nucleotide sequences which encode a polypeptide having the amino acid sequence of SEQ ID NO:2 or the mature polypeptide thereof, which differs from SEQ ID NO:1 by virtue of the degeneracy of the genetic code. The present invention also relates to subsequences of SEQ ID NO:1 which encode fragments of SEQ ID NO:2 that have endoglucanase activity, such as the catalytic core domain of amino acid 65 to 347 of SEQ ID NO:2 or the fragment of amino acid 368 to 569 of SEQ ID NO:2.

The present invention also relates to mutant polynucleotides comprising at least one mutation in the mature polypeptide coding sequence of SEQ ID NO:1, in which the mutant nucleotide sequence encodes a polypeptide which consists of amino acids 1 to 759 of SEQ ID NO:2.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Bacillus*, or another or related organism and thus, for example, may be an allelic or species variant of the polypeptide encoding region of the nucleotide sequence.

The present invention also relates to polynucleotides having nucleotide sequences which have a degree of identity to the mature polypeptide coding sequence of SEQ ID NO:1 (i.e., nucleotides 100 to 2376) of at least 60%, preferably at least 65%, more preferably at least 70%, more preferably at least 75%, more preferably at least 80%, more preferably at least 85%, more preferably at least 90%, even more preferably at least 95%, and most preferably at least 97% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the polypeptide encoding region of SEQ ID NO:1, e.g., a subsequence thereof, and/or by introduction of nucleotide substitutions which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for endoglucanase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The present invention also relates to isolated polynucleotides encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 100 to 2376 of SEQ ID NO:1, (ii) nucleotides 193 to 1041 of SEQ ID NO:1, (iii) nucleotides 1104 to 1707 of SEQ ID NO:1 or (iv) a complementary strand of (i) to (iii); or allelic variants and subsequences thereof (Sambrook et al., 1989, supra), as defined herein.

The present invention also relates to isolated polynucleotides obtained by (a) hybridizing a population of DNA under very low, low, medium, medium-high, high, or very high stringency conditions with (i) nucleotides 100 to 2376 of SEQ ID NO:1, or (ii) a complementary strand of (i); and (b) isolating the hybridizing polynucleotide, which encodes a polypeptide having endoglucanase activity.

Nucleic Acid Constructs

The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydro-genase (ADH1,ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

In a preferred aspect, the signal peptide coding region is nucleotides 1 to 99 of SEQ ID NO:1 which encode amino acids −33 to −1 of SEQ ID NO:2.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

A conditionally essential gene may function as a non-antibiotic selectable marker. Non-limiting examples of bacterial conditionally essential non-antibiotic selectable markers are the dal genes from *Bacillus subtilis, Bacillus licheniformis*, or other Bacilli, that are only essential when the bacterium is cultivated in the absence of D-alanine. Also the genes encoding enzymes involved in the turnover of UDP-galactose can function as conditionally essential markers in a cell when the cell is grown in the presence of galactose or grown in a medium which gives rise to the presence of galactose. Non-limiting examples of such genes are those from *B. subtilis* or *B. licheniformis* encoding UTP-dependent phosphorylase (EC 2.7.7.10), UDP-glucose-dependent uridylyltransferase (EC 2.7.7.12), or UDP-galactose epimerase (EC 5.1.3.2). Also a xylose isomerase gene such as xylA, of Bacilli can be used as selectable markers in cells grown in minimal medium with xylose as sole carbon source. The genes necessary for utilizing gluconate, gntK, and gntP can also be used as selectable markers in cells grown in minimal medium with gluconate as sole carbon source. Other examples of conditionally essential genes are known in the art. Antibiotic selectable markers confer antibiotic resistance to such antibiotics as ampicillin, kanamycin, chloramphenicol, erythromycin, tetracycline, neomycin, hygromycin or methotrexate.

Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus, Bacillus licheniformis, Bacillus stearothermophilus*, or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, *Soc. App. Bacteriol. Symposium Series* No. 9, 1980).

In an even more preferred aspect, the yeast host cell is a *Candida, Hansenula, Kluyveromyces, Pichia, Saccharomyces, Schizosaccharomyces,* or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filobasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa,* or *Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* strain cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention, comprising (a) cultivating a cell, which in its wild-type form is capable of producing the polypeptide, under conditions conducive for production of the polypeptide; and (b) recovering the polypeptide. Preferably, the cell is of the genus *Bacillus*.

The present invention also relates to methods for producing a polypeptide of the present invention, comprising (a) cultivating a host cell under conditions conducive for production of the polypeptide; and (b) recovering the polypeptide.

The present invention also relates to methods for producing a polypeptide of the present invention, comprising (a) cultivating a host cell under conditions conducive for production of the polypeptide, wherein the host cell comprises a mutant nucleotide sequence having at least one mutation in the mature polypeptide coding region of SEQ ID NO: 1, wherein the mutant nucleotide sequence encodes a polypeptide which comprises amino acids 1-759 of SEQ ID NO:2, or amino acids 65 to 347 of SEQ ID NO:2 or amino acids 368 to 569 of SEQ ID NO:2, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

The present invention also relates to isolated enzymes having endo-beta-1,4-glucanse activity and which are produced by one of the above mentioned methods, preferably by recombinant production techniques. The isolated enzymes are preferably free from homologous impurities. Such impurities may arise from endogenous endo-beta-1,4-glucanse genes, hence if production is performed in a host cell which does not express endogenous polypeptides with endo-beta-1,4-glucanse activity, the enzyme will be free of homologous impurities.

Compositions

The present invention also relates to compositions comprising a polypeptide of the present invention. Preferably, the compositions are enriched in such a polypeptide. The term "enriched" indicates that the endoglucanase activity of the composition has been increased, e.g., with an enrichment factor of 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiatum*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

Textile Applications

In another embodiment, the present invention relates to use of the endoglucanase of the invention in textile finishing processes, such as bio-polishing. Bio-polishing is a specific treatment of the yarn surface which improves fabric quality with respect to handle and appearance without loss of fabric wettability. The most important effects of bio-polishing can be characterized by less fuzz and pilling, increased gloss/luster, improved fabric handle, increased durable softness and altered water absorbency. Bio-polishing usually takes place in the wet processing during the manufacture of knitted and woven fabrics. Wet processing comprises such steps as, e.g., desizing, scouring, bleaching, washing, dying/printing and finishing. During each of these steps, the fabric is more or less subjected to mechanical action. In general, after the textiles have been knitted or woven, the fabric proceeds to an optional desizing stage, followed by a scouring stage, etc. Desizing is the act of removing size from textiles. Prior to weaving on mechanical looms, warp yarns are often coated with size consisting of starch or starch derivatives in order to increase their tensile strength. After weaving, the size coating must be removed before further processing of the fabric in order to ensure a homogeneous and wash-proof result. In the scouring process impurities are removed from the fabric. The endoglucanase of the invention can advantageously be used in the scouring of cellulosic and cotton textiles, as well as bast fibers and may improve efficiency of removal of impurities.

One of the most commonly used methods for delivering durable press to cellulosic textiles is via finishing with cellulose crosslinking chemistry. Crosslinking immobilizes cellulose at a molecular level and substantially reduces shrinking and wrinkling of cellulosic garments. Treatment of durable press treated cellulosic textiles with the endo-glucanase of the invention may result in a selective relaxation of stressed regions to minimize edge abrasion.

Additionally, the endoglucanase of the invention can be used to efficiently remove excess carboxymethyl cellulose-based print paste from textile and equipment used in the printing process.

It is known that in order to achieve the effects of bio-polishing, a combination of cellulolytic and mechanical action is required. It is also known that "super-softness" is achievable when the treatment with a cellulase is combined with a conventional treatment with softening agents. It is contemplated that use of the endoglucanase of the invention and of combinations of this enzyme with other enzymes for bio-polishing of cellulosics (natural and manufactured cellulosics, fabrics, garments, yarns, and fibers) is advantageous, e.g., a more thorough polishing can be achieved. It is believed that bio-polishing may be obtained by applying the method described, e.g., in WO 93/20278. It is further contemplated that the endoglucanase of the invention can be applied to simultaneous or sequential textile wet processes, including different combinations of desizing, scouring, bleaching, bio-polishing, dyeing, and finishing.

Stone-Washing

It is known that a "stone-washed" look (localized abrasion of the color) in dyed fabric, especially in denim fabric or jeans, can be provided either by washing the denim or jeans made from such fabric in the presence of pumice stones to provide the desired localized lightening of the color of the fabric or by treating the fabric enzymatically, in particular with cellulytic enzymes. The treatment with an endoglucanase of the present invention, alone or in combination with other enzymes, may be carried out either alone such as disclosed in U.S. Pat. No. 4,832,864, together with a smaller amount of pumice than required in the traditional process, or together with perlite such as disclosed in WO 95/09225. Treatment of denim fabric with the endoglucanase of the invention may reduce backstaining compared to conventional methods.

Biomass Degradation

The enzyme or the enzyme composition according to the invention may be applied advantageously, e.g., as follows:

For debarking, i.e., pre-treatment with hydrolytic enzymes which may partly degrade the pectin-rich cambium layer prior to debarking in mechanical drums resulting in advantageous energy savings.

For defibration (refining or beating), i.e., treatment of material containing cellulosic fibers with hydrolytic enzymes prior to the refining or beating which results in reduction of the energy consumption due to the hydrolysing effect of the enzymes on the surfaces of the fibers.

For fiber modification, i.e., improvement of fibre properties where partial hydrolysis across the fibre wall is needed which requires deeper penetrating enzymes (e.g., in order to make coarse fibers more flexible).

For drainage: The drainability of papermaking pulps may be improved by treatment of the pulp with hydrolysing enzymes. Use of the enzyme or enzyme composition of to the invention may be more effective, e.g., result in a higher degree of loosening bundles of strongly hydrated micro-fibrils in the fines fraction that limits the rate of drainage by blocking hollow spaces between the fibers and in the wire mesh of the paper machine.

The treatment of lignocellulosic pulp may, e.g., be performed as described in WO 93/08275, WO 91/02839 and WO 92/03608.

Laundry

The enzyme or enzyme composition of the invention may be useful in a detergent composition for household or industrial laundering of textiles and garments, and in a process for machine wash treatment of fabrics comprising treating the fabrics during one or more washing cycle of a machine washing process with a washing solution containing the enzyme or enzyme preparation of the invention.

Typically, the detergent composition used in the washing process comprises conventional ingredients such as surfactants (anionic, nonionic, zwitterionic, amphoteric), builders, bleaches (perborates, percarbonates or hydrogen peroxide) and other ingredients, e.g., as described in WO 97/01629 which is hereby incorporated by reference in its entirety.

Detergent Applications

The enzyme of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations, especially for automatic dish washing (ADW).

The endo-beta-1,4-glucanase of the invention provides advantages such as improved stain removal and decreased soil redeposition. Certain stains, for example certain food stains, contain beta-glucans which make complete removal of the stain difficult to achieve. Also, the cellulosic fibres of the fabrics may possess, particularly in the "non-crystalline" and surface regions, beta-glucan polymers that are degraded by this enzyme. Hydrolysis of such beta-glucans, either in the stain or on the fabric, during the washing process decreases the binding of soils onto the fabrics.

Household laundry processes are carried out under a range of conditions. Commonly, the washing time is from 5 to 60 minutes and the washing temperature is in the range 15-60° C., most commonly from 20-40° C. The washing solution is normally neutral or alkaline, most commonly with pH 7-10.5. Bleaches are commonly used, particularly for laundry of white fabrics. These bleaches are commonly the peroxide bleaches, such as sodium perborate, sodium percarbonate or hydrogen peroxide.

In a specific aspect, the invention provides a detergent additive comprising the enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Relase®, Alcalase®, Savinase®, Primase®, Everlase®, Esperase®, Ovozyme®, Coronase®, Polarzyme® and Kannase® (Novozymes A/S), Maxatase™, Maxacal™, Maxapem™, Properase™, Purafect™, Purafect OxP™, FN2™, FN3™, FN4™ and Purafect Prime™ (Genencor International, Inc.), BLAP X and BLAP S (Henkel).

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202. Preferred commercially available lipase enzymes include Lipolase™ and Lipolase Ultra™ (Novozymes A/S).

Amylases: Suitable amylases (α and/or β) include those of bacterial or fungal origin. Chemically modified or protein engineered mutants are included. Amylases include, for example, α-amylases obtained from *Bacillus*, e.g., a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially used amylases are Duramyl®, Termamyl®, Stainzyme®, Fungamyl® and BAN® (Novozymes A/S), Rapidase™, Purastar™ and Purastar OxAm™ (from Genencor International Inc.).

Cellulases: Other suitable cellulases include those of bacterial or fungal origin. Chemically modified or protein engineered mutants are included. Suitable cellulases include cellulases from the genera *Bacillus*, *Pseudomonas*, *Humicola*, *Fusarium*, *Thielavia*, *Acremonium*, e.g., the fungal cellulases produced from *Humicola insolens*, *Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and WO 99/01544.

Commercially available cellulases include Celluzyme™, Renozyme® and Carezyme™ (Novozymes A/S), Clazinase™, and Puradax HA™ (Genencor International Inc.), and KAC-500(B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

Hemicellulases: Suitable hemicellulases include those of bacterial or fungal origin. Chemically modified or protein engineered mutants are included. Suitable hemicellulases include mannanase, lichenase, xylanase, arabinase, galactanase acetyl xylan esterase, glucorunidase, ferulic acid esterase, coumaric acid esterase and arabinofuranosidase as described in WO 95/35362. Suitable mannanases are described in WO 99/64619.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, e.g., as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethyl-cellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, e.g., the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bacteriocides, optical brighteners, hydrotropes, tarnish inhibitors, or perfumes.

In the detergent compositions any enzyme, in particular the enzyme of the invention, may be added in an amount corresponding to 0.01-100 mg of enzyme protein per litre of wash liquor, preferably 0.05-5 mg of enzyme protein per litre of wash liquor, in particular 0.1-1 mg of enzyme protein per litre of wash liquor.

The enzyme of the invention may additionally be incorporated in the detergent formulations disclosed in WO 97/07202 which is hereby incorporated as reference.

Signal Peptide and Propeptide

The present invention also relates to nucleic acid constructs comprising a gene encoding a protein operably linked to a nucleotide sequence encoding a signal peptide, wherein the gene is foreign to the nucleotide sequence encoding a signal peptide.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The first and second nucleotide sequences may be operably linked to foreign genes individually with other control sequences or in combination with other control sequences. Such other control sequences are described supra. As described earlier, where both signal peptide and propeptide regions are present at the amino terminus of a protein, the propeptide region is positioned next to the amino terminus of a protein and the signal peptide region is positioned next to the amino terminus of the propeptide region.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Chemicals used as buffers and substrates were commercial products of at least reagent grade.
Endoglucanase Activity Assay
Materials:
Berol 537, nonionic surfactant supplied by Akzo Nobel, or similar.
Cellazyme C tablets, supplied by Megazyme International, Ireland.
Glass microfiber filters, GF/C, 9 cm diameter, supplied by Whatman.
pH 9.5 Buffer Solution:
Dissolve 21.0 g of $NaHCO_3$ and 14.6 g of NaCl in about 900 ml of deionised water. Add 10 ml Berol 537 (nonionic surfactant supplied by Akzo Nobel). Adjust the pH to 9.5 by addition of 4 N NaOH. Then adjust the final volume to 1000 ml.
Method:
In test tubes, mix 1 ml pH 9.5 buffer and 5 ml deionised water.
Add 100 microliters of the enzyme sample (or of dilutions of the enzyme sample with known weight:weight dilution factor). Add 1 Cellazyme C tablet into each tube, cap the tubes and mix on a vortex mixer for 10 seconds. Place the tubes in a thermostated water bath, temperature 40° C. After 15, 30 and 45 minutes, mix the contents of the tubes by inverting the tubes, and replace in the water bath. After 60 minutes, mix the contents of the tubes by inversion and then filter through a GF/C filter. Collect the filtrate in clean tubes.

Measure Absorbance ($A_{enz}$) at 590 nm, with a spectrophotometer. A blank value, $A_{water}$, is determined by adding 100 microliters water instead of 100 microliters enzyme dilution.

Calculate $A_{delta} = A_{enz} - A_{water}$.

$A_{delta}$ must be <0.5. If higher results are obtained, repeat with a different enzyme dilution factor. Determine DF0.1, where DF0.1 is the dilution factor needed to give $A_{delta} = 0.1$.

Unit Definition:

1 Endo-Beta-Glucanase activity unit (1 EBG) is the amount of enzyme that gives $A_{delta} = 0.10$, under the assay conditions specified above. Thus, for example, if a given enzyme sample, after dilution by a dilution factor of 100, gives $A_{delta} = 0.10$, then the enzyme sample has an activity of 100 EBG/g.

Temperature and pH optima of the endoglucanase are determined by running the activity assay at a range of different temperatures when the pH is fixed and vice versa a range of different pH's when the temperature is fixed.

Example 1

Screening for Novel Endoglucanase

A number of *Bacillus* strains were screened for production of alkaline endoglucanase by growing the bacteria on TY agar added 0.1% AZCL-betaglucan (barley, Megazyme). Strain ACE160 produced blue haloes on this substrate, the bacterium was identified by determination of a part of the 16S rDNA, and insertion of the sequence in the phylogenetic tree showed that ACE160 represent a new species with the *Bacillus* group.

Example 2

Production of Full Length Endoglucanase

Genomic Library Construction

Chromosomal DNA from ACE160 was prepared by using standard molecular biology techniques (Ausuble et al. 1995 "Current protocols in molecular biology" Publ: John Wiley and sons). The prepared DNA was partially cleaved with Sau3A and separated on an agarose gel. Fragments of 3 to 8 kilobases were eluted and precipitated and resuspended in a suitable buffer.

A genomic library was made by using the Stratagene ZAP Express™ predigested Vector kit and Stratagene ZAP Express™ predigested Gigapack® cloning kit (Bam HI predigested) (Stratagene Inc., USA) following the instructions/recommendations from the vendor. The resulting lambdaZAP library comprised 38000 pfu (plaque forming units) of which 10000 were collected for mass excision. The resulting 70000 *E. coli* colonies were pooled. The *E. coli* clone pool was diluted by mixing 100 microliters pool with 100 ml LB medium and plated out 100 microliters per agarplate on LB supplemented with 0.1% AZCL.betaglucan (barley, Megazyme) and 50 micrograms/ml kanamycin, and incubated for 2-3 days. Among 1600-1800 colonies per plate on 50 agarplates three colonies with blue haloes were obtained. From these three colonies plasmid DNA was recovered and sequenced with vector primers.

By subsequent primer walking the entire nucleotide sequence of the endo-1,4-betaglucanase open reading frame (ORF) was characterized. The three colonies contained the same ORF shown as SEQ ID NO:1.

Production of the Full Length Endoglucanase

To produce the endo-1,4-betaglucanase, the gene was amplified from chromosomal DNA of the wild type strain *Bacillus* sp. ACE160. The enzymes were expressed using the indigenous trans membrane signal peptide.

Primers

```
ACE160-Bglu-Mlu1-4:
                                    (SEQ ID NO: 3)
GATTAACGCGTTCCTCGTGCTGAGCACAGAGG ACE160-Bglu-Sac1:
                                    (SEQ ID NO: 4)
TTATGGAGCTCAAATCAACTCTAGGAGGCTG
```

The endo-1,4-betaglucanase gene was amplified as a ca. 2500 nt PCR product. The primers ACE160-Bglu-Sac1 and ACE160-Bglu-Mlu1-4 were used. Template DNA was chromosomal DNA of *Bacillus* sp. ACE160. The PCR product was recovered using Qiaquick™ spin columns as recommended (Qiagen, Germany). The quality of the isolated template was evaluated by agarose gel electrophoresis. PCR was run in the following protocol: 94° C., 2 minutes 40 cycles of [94° C. for 30 seconds, 52° C. for 30 seconds, 68° C. for 1 minute] completed with 68° C. for 10 minutes. PCR product was analysed on a 1% agarose gel in TAE buffer stained with Ethidium bromide to confirm a single band of the correct size. The PCR product was digested with restriction enzymes SacI and Mlu1 and purified on GFX™ PCR and Gel Band Purification Kit (Amerham Biosciences).

The digested and purified PCR fragment was ligated to the Sac I and Mlu I digested plasmid pDG268NeoMCS-PramyQ/PrcryIII/cryIIIAstab/Sav (U.S. Pat. No. 5,955,310).

The ligation mixture was used for transformation into *E. coli* TOP10F' (Invitrogen BV, The Netherlands) and several colonies were selected for miniprep (QIAprep® spin, QIAGEN GmbH, Germany). The purified plasmids were checked for insert before transformation into *Bacillus subtilis* strain TH1 (TH1 is a *Bacillus subtilis* strain (amy-,spo-,apr-,npr-), that has been modified by insertion of a construct, from the strain DN3 (Noone et al., 2000, *J. Bacteriol.* 182(6): 1592-1599) by transformation and selection for erytromycin. The changed genotype is: ykdA::pDN3 (PykdA-lacZ Pspac-ykdA) Ermr. TH1 contains the following features: the full ykdA promoter is fused to the LacZ reporter gene. In addition the ykdA gene is placed under control of the IPTG-inducible Pspac promoter, so the ykdA gene no longer has it's naturally regulation. The strain can be used as host for expression clones and libraries and transformants expressing and secreting protein can be selected on plates containing X-gal and IPTG. TH1 can be maintained on LB agar +6 micrograms/mL erythromycin).

Transformed cells were plated on LB-PG agar plates, supplemented with 1% skim milk, 100 micrograms/L X-gal, 1 mM IPTG, 6 micrograms/ml chloramphenicol and 12 micrograms/ml erythromycin. The plated cells were incubated over night at 37° C. and colonies with blue color and without clearing zone were picked, the correct insert was confirmed by PCR and nucleotide sequencing.

Example 3

Purification of the Endoglucanase from *Bacillus* sp. ACE160

The endoglucanase was purified from 670 ml fermentation broth from which the cells were removed by a combination of centrifugation and filtration of the broth. The volume was adjusted to 2 l with deionised water and the pH titrated to 8.5. This material was loaded on a Q-sparse column equilibrated with 25 mM Tries buffer pH 8.5. The enzyme was eluted by the application of a NaCl gradient in the same buffer and the fractions containing the endoglucanase were pooled. A portion of this pool was fractionated on a S-200 gel filtration column with 100 mM sodium acetate pH 6 as the liquid phase. The fractions containing the endoglucanase were pooled and concentrated about three times on an Am icon ultra filtration unit. The concentrate was analyzed by SDS PAGE, where a protein band of app. 80 kid was obtained.

Example 4

Wash Performance of Endoglucanase from *Bacillus* sp. ACE160

This procedure is used to determine the "enzyme detergency benefit".

The wash tests are made by washing samples of soiled cotton fabric and samples of clean cotton fabric, both together, in a small-scale wash test apparatus. After the washing the soil on the cotton fabric is evaluated by light reflectance. Both the originally soiled cotton fabric and the originally clean cotton fabric samples are evaluated.

Cotton fabric: #2003 white woven 100% cotton fabric, supplied by Tanigashira, 4-11-15 Komatsu Yodogawa-ku, Osaka, 533-0004, Japan. The new cotton fabric is pre-washed three times before use in the wash test. The pre-washing is done using a European household front-loader washing machine, and using a standard 40° C. wash process. LAS (Surfac® SDBS80 sodium alkylbenzene sulfonate, 80%) is added to the wash water at concentration 0.5 g per liter and the wash solution pH is adjusted to 10 by addition of sodium carbonate. After the pre-washing the fabric is dried in a tumbler drier. Swatches of the pre-washed cotton fabric, size 5 cm×5 cm, weight approximately 0.3 g each, are cut out and these swatches are used for the wash tests.

Soiled cotton swatches: These are prepared from the 5 cm×5 cm swatches described above. Soiled swatches are made using beta-glucan (medium viscosity, from barley, supplied by Megazymes International, Ireland) and carbon black ("carbon for detergency tests", supplied by Sentaku Kagaku Kyokai, Tokyo, Japan). Dissolve about 0.67 g of beta-glucan in 100 ml tap water by stirring and warming to >50° C. Add 0.33 g carbon black. Blend with an UltraTurrax T25 blender, speed 4000 rpm for 2 minutes. Apply 250 microliters of the beta-glucan/carbon onto the center of each swatch. Allow to dry overnight at room temperature.

Wash tests: Three soiled swatches and three clean swatches are washed in a Mini-Terg-O-Tometer machine. The Mini-Terg-O-Tometer is a small-scale version of the Terg-O-Tometer test washing machine described in Jay C. Harris, "Detergency Evaluation and Testing", Interscience Publishers Ltd. (1954) pp. 60-61. The following conditions are used:

| | |
|---|---|
| Beaker size | 250 ml |
| Wash solution volume | 100 ml |
| Wash temperature | 40° C. |
| Wash time | 30 minutes |
| Agitation | 150 rpm |

The detergent solutions are pre-warmed to 40° C. before starting the test. The fabric and the enzymes are added at the start of the 30 minute wash period. After the wash, the fabric swatches are rinsed for 5 minutes under running tap water, then spread out flat and allowed to air dry at room temperature overnight.

Instrumental evaluations: Light reflectance evaluation of the fabric swatches is done using a Macbeth Color Eye 7000 reflectance spectrophotometer. The measurements are made at 500 nm. The UV filter is not included. Measurements are made on the front and back of each swatch. The soiled swatches are measured in the centre of the soiled area. Average results for reflectance (R, 500 nm) for the soiled swatches and for the clean swatches are then calculated from the six measurements on each type.

Detergent solutions: Detergent solutions are prepared as follows: To prepare 1 liter of solution, dissolve in deionized water 0.5 g sodium carbonate and 1.0 g sodium hydrogen carbonate and add 2 ml of a solution containing 117.8 g/l $CaCl_2.2H_2O$ and 54.3 g/l $MgCl_2.6H_2O$. This calcium/magnesium addition provides a water hardness of 12° dH. Add 0.2 g nonionic surfactant (Berol® 537, Akzo Nobel) and 0.5 g LAS (Surfac® SDBS80 sodium alkylbenzene sulfonate, 80%) and adjust the final volume to 1 liter. Adjust the pH to pH 9.5±0.1 (by addition of sodium carbonate or 10% citric acid solution).

Enzyme addition: The enzymes to be tested are pre-dissolved at known concentrations in water, and the required amount of enzyme is added to the detergent solution at the start of the wash process.

Calculation of enzyme detergency benefit: The enzyme detergency benefit is a measure of how much more clean the swatches, both the originally soiled and the originally clean, become as a result of including enzymes in the wash test. The enzyme detergency benefit is calculated as follows:

After the wash test the average R, 500 nm value for the soiled swatches is R, soiled.

After the wash test the average R, 500 nm value for the clean swatches is R, clean.

The enzyme detergency benefit from a wash test with enzymes is the sum of R, soiled +R, clean with enzymes minus the sum of R, soiled +R, clean with no added enzyme.

The enzyme detergency benefit value determined in this way is a combined measure both of the removal of soil from the fabric and of the redeposition of soil onto the fabric. Thus the enzyme detergency benefit value can have values that are negative or positive. The enzyme detergency benefit value can be used to compare the performance of different enzymes. The highest positive detergency benefit value is the preferred result. For comparison, the wash performance of the endoglucanase from *Bacillus* sp. ACE160 was compared with of the wash performance of the prior art *Bacillus* endoglucanase MB1181-7 disclosed in WO 2002/099091.

Results:

| Enzyme activity in wash solution | Enzyme Detergency Benefit |
|---|---|
| ACE160, 6 EBG per liter | 28.1 |
| ACE160, 12 EBG per liter | 29.9 |
| MB1181-7, 6 EBG per liter | 15.2 |
| MB1181-7, 12 EBG per liter | 22.2 |

The results show that the endoglucanase from *Bacillus* sp. ACE160 gives a higher Enzyme Detergency Benefit than the known endoglucanase.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. An isolated polypeptide having endoglucanase activity, selected from the group consisting of:
   a) a polypeptide with at least 95% sequence identity to the sequence of amino acids 1 to 759 of SEQ ID NO: 2;
   b) a polypeptide which is encoded by a polynucleotide which hybridizes under high stringency conditions with (i) nucleotides 100 to 2376 of SEQ ID NO: 1, (ii) nucleotides 193 to 1041 of SEQ ID NO: 1, or (iii) the full length complementary strand of (i) or (ii), wherein the high stringency conditions are defined as prehybridization and hybridization at 42° C. in 5×SSPE, 0.3% SDS, 200 micrograms/ml sheared and denatured salmon sperm DNA, and 50% formamide, following standard Southern blotting procedures, following by washing three times each for 15 minutes using 2×SSC, 0.2% SDS at 65° C.; and
   c) a fragment of amino acids 1 to 759 of SEQ ID NO: 2 having endoglucanase activity.

2. The polypeptide of claim 1, which has at least 95% sequence identity to the sequence of amino acids 1 to 759 of SEQ ID NO: 2.

3. The polypeptide of claim 1, which has at least 97% sequence identity to the sequence of amino acids 1 to 759 of SEQ ID NO: 2.

4. The polypeptide of claim 1, which has 100% sequence identity to the sequence of amino acids 1 to 759 of SEQ ID NO: 2.

5. The polypeptide of claim 1, which comprises the sequence of amino acids 1 to 759 of SEQ ID NO: 2.

6. The polypeptide of claim 1, which is encoded by a polynucleotide which hybridizes under the high stringency conditions with (i) nucleotides 100 to 2376 of SEQ ID NO: 1, (ii) nucleotides 193 to 1041 of SEQ ID NO: 1, or (iii) the full length complementary strand of (i) or (ii).

7. The polypeptide of claim 1, which is encoded by a polynucleotide which hybridizes under very high stringency conditions with (i) nucleotides 100 to 2376 of SEQ ID NO: 1, (ii) nucleotides 193 to 1041 of SEQ ID NO: 1, or (iii) the full length complementary strand of (i) or (ii), wherein the very high stringency conditions are defined as prehybridization and hybridization at 42° C. in 5×SSPE, 0.3% SDS, 200 micrograms/ml sheared and denatured salmon sperm DNA, and 50% formamide, following standard Southern blotting procedures, following by washing three times each for 15 minutes using 2×SSC, 0.2% SDS at 70° C.

8. The polypeptide of claim 1, which is a fragment of amino acids 1 to 759 of SEQ ID NO: 2 having endoglucanase activity.

9. The polypeptide of claim 1, which has at least one of the following properties:
   a) a pI of 4.4,
   b) a pH optimum of 9,
   c) a temperature optimum of 40° C., or
   d) stability at pH from 5 to 10.5.

10. A composition comprising a polypeptide of claim 1.

11. The composition of claim 10, which further comprises one or more enzymes selected from the group consisting of alpha-amylases, cellulases, cutinases, glucoamylases, hemicellulases, laccases, ligninases, lipases, mannanases, oxidases, pectate lyases, pectin acetyl esterases, pectinases, pectin lyases, pectin methylesterases, peroxidases, phenoloxidases, polygalacturonases, proteases, pullulanases, reductases, rhamnogalacturonases, transglutaminases, xylanases, and xyloglucanases.

12. A detergent composition comprising a polypeptide of claim 1 and a surfactant.

13. A method for degrading cellulose-containing biomass, comprising treating the biomass with an effective amount of a polypeptide of claim 1.

14. An isolated polypeptide having endoglucanase activity, which comprises a catalytic domain with at least 95% sequence identity to the sequence of amino acids 65 to 347 of SEQ ID NO: 2, wherein the catalytic domain has endoglucanase activity.

15. The polypeptide of claim 14, wherein the catalytic domain has at least 98% sequence identity to the sequence of amino acids 65 to 347 of SEQ ID NO: 2.

16. The polypeptide of claim 14, wherein the catalytic domain has 100% sequence identity to the sequence of amino acids 65 to 347 of SEQ ID NO: 2.

17. The polypeptide of claim 14, wherein the catalytic domain comprises the sequence of amino acids 65 to 347 of SEQ ID NO: 2.

18. A composition comprising a polypeptide of claim 4.

19. The composition of claim 18, which further comprises one or more enzymes selected from the group consisting of alpha-amylases, cellulases, cutinases, glucoamylases, hemicellulases, laccases, ligninases, lipases, mannanases, oxidases, pectate lyases, pectin acetyl esterases, pectinases, pectin lyases, pectin methylesterases, peroxidases, phenoloxidases, polygalacturonases, proteases, pullulanases, reductases, rhamnogalacturonases, transglutaminases, xylanases, and xyloglucanases.

20. A detergent composition comprising a polypeptide of claim 14 and a surfactant.

21. A method for degrading cellulose-containing biomass, comprising treating the biomass with an effective amount of a polypeptide of claim 14.

22. An isolated polypeptide having endoglucanase activity, which comprises a catalytic domain and a carbohydrate binding module, wherein the cataltic domain domain has endoglucanase activity and the carbohydrate binding module has at least 95% sequence identity to the sequence of amino acids 368 to 569 of SEQ ID NO: 2 and has carbohydrate binding activity.

23. The polypeptide of claim 22, wherein the carbohydrate binding module has at least 97% sequence identity to the sequence of amino acids 368 to 569 of SEQ ID NO: 2.

24. The polypeptide of claim 22, wherein the carbohydrate binding module has 100% sequence identity to the sequence of amino acids 368 to 569 of SEQ ID NO: 2.

25. The polypeptide of claim 22, wherein the carbohydrate binding module comprises the sequence of amino acids 368 to 569 of SEQ ID NO: 2.

26. A composition comprising a polypeptide of claim 22.

27. The composition of claim 22, which further comprises one or more enzymes selected from the group consisting of alpha-amylases, cellulases, cutinases, glucoamylases, hemicellulases, laccases, ligninases, lipases, mannanases, oxidases, pectate lyases, pectin acetyl esterases, pectinases, pectin lyases, pectin methylesterases, peroxidases, phenoloxidases, polygalacturonases, proteases, pullulanases, reductases, rhamnogalacturonases, transglutaminases, xylanases, and xyloglucanases.

28. A detergent composition comprising a polypeptide of claim 22 and a surfactant.

29. A method for degrading cellulose-containing biomass, comprising treating the biomass with an effective amount of a polypeptide of claim 22.

* * * * *

UNITED STATES PATENT AND TRADEMARK OFFICE
CERTIFICATE OF CORRECTION

PATENT NO. : 8,309,338 B2
APPLICATION NO. : 13/093350
DATED : November 13, 2012
INVENTOR(S) : Johansen et al.

Page 1 of 1

It is certified that error appears in the above-identified patent and that said Letters Patent is hereby corrected as shown below:

Column 72, line 5, please delete "claim 22" and insert --claim 26--.

Signed and Sealed this
Second Day of April, 2013

Teresa Stanek Rea
*Acting Director of the United States Patent and Trademark Office*

SEQUENCE LISTING

```
<160> NUMBER OF SEQ ID NOS: 10

<210> SEQ ID NO 1
<211> LENGTH: 2379
<212> TYPE: DNA
<213> ORGANISM: Bacillus sp. ACE160
<220> FEATURE:
<221> NAME/KEY: CDS
<222> LOCATION: (1)..(2376)
<220> FEATURE:
<221> NAME/KEY: sig_peptide
<222> LOCATION: (1)..(99)
<220> FEATURE:
<221> NAME/KEY: mat_peptide
<222> LOCATION: (100)..(2376)

<400> SEQUENCE: 1 gtg aga caa ccc ata ggt aaa aag ata att gct gca gga atg atc ttt        48
Val Arg Gln Pro Ile Gly Lys Lys Ile Ile Ala Ala Gly Met Ile Phe
            -30                 -25                 -20 acc ctc tta ttt tcg tta atc gtc act gtg ttc cca act gct ggt caa       96
Thr Leu Leu Phe Ser Leu Ile Val Thr Val Phe Pro Thr Ala Gly Gln
        -15                 -10                  -5 gca cta gaa tca gac tat agc cat tta tta gga aat gat gca gtg aag      144
Ala Leu Glu Ser Asp Tyr Ser His Leu Leu Gly Asn Asp Ala Val Lys
-1   1               5                  10                  15 cgc ccc tcg gaa ggc gga gct tta agt tta tgt aat gaa act act cca      192
Arg Pro Ser Glu Gly Gly Ala Leu Ser Leu Cys Asn Glu Thr Thr Pro
                20                  25                  30 gta aaa cca aac cat gcg ggg gac cgt ggg aaa cca agc cac gca ggt      240
Val Lys Pro Asn His Ala Gly Asp Arg Gly Lys Pro Ser His Ala Gly
                35                  40                  45 aaa gga aag cct ccc cat gct ggt aag cct gaa cat gcc gga cca aag      288
Lys Gly Lys Pro Pro His Ala Gly Lys Pro Glu His Ala Gly Pro Lys
            50                  55                  60 cgt aaa aca ctg tgt gat gca acc ggc agc caa att cag ctc cgg ggg      336
Arg Lys Thr Leu Cys Asp Ala Thr Gly Ser Gln Ile Gln Leu Arg Gly
        65                  70                  75 atg agc act cac gga ttg caa tgg ttt ggc gag att ata aat gat aat      384
Met Ser Thr His Gly Leu Gln Trp Phe Gly Glu Ile Ile Asn Asp Asn
80                  85                  90                  95 gct ttt gct gct ctt tcc aac gac tgg gag gca aat atg atc cgc ctt      432
Ala Phe Ala Ala Leu Ser Asn Asp Trp Glu Ala Asn Met Ile Arg Leu
                100                 105                 110 gcc atg tat att ggc gaa aat gga tat gcg act aac cct gaa gta aaa      480
Ala Met Tyr Ile Gly Glu Asn Gly Tyr Ala Thr Asn Pro Glu Val Lys
            115                 120                 125 gaa ctt gtt tac gaa gga att gag ctt gca ttc aaa cat gat atg tat      528
Glu Leu Val Tyr Glu Gly Ile Glu Leu Ala Phe Lys His Asp Met Tyr
        130                 135                 140 gta att gtt gac tgg cac gta cac gcc ccg gga gat cca agg gct gac      576
Val Ile Val Asp Trp His Val His Ala Pro Gly Asp Pro Arg Ala Asp
    145                 150                 155 att tat tcc ggt gct cta gac ttt ttt aaa gaa att gca gac cac tat      624
Ile Tyr Ser Gly Ala Leu Asp Phe Phe Lys Glu Ile Ala Asp His Tyr
160                 165                 170                 175
```

```
aag gac cat cct aag ttc cat tat att ata tgg gaa att gca aat gaa    672
Lys Asp His Pro Lys Phe His Tyr Ile Ile Trp Glu Ile Ala Asn Glu
            180                 185                 190 cca agc cca aat aac agc gga gga cct gga att cct aat gat gaa aca    720
Pro Ser Pro Asn Asn Ser Gly Gly Pro Gly Ile Pro Asn Asp Glu Thr
            195                 200                 205 gga tgg aaa gca gta aag gaa tat gct gaa cct atc gtg gaa atg ctt    768
Gly Trp Lys Ala Val Lys Glu Tyr Ala Glu Pro Ile Val Glu Met Leu
            210                 215                 220 cgt gaa agg ggg gac aat ata att ctt gta ggc agc ccg aac tgg agc    816
Arg Glu Arg Gly Asp Asn Ile Ile Leu Val Gly Ser Pro Asn Trp Ser
225                 230                 235 cag cgc ccg gat tta gct gca gat aac cct ata gat gca aaa aat atc    864
Gln Arg Pro Asp Leu Ala Ala Asp Asn Pro Ile Asp Ala Lys Asn Ile
240                 245                 250                 255 atg tac tct gtc cac ttc tat act gga tct cat gaa cct tca gat aca    912
Met Tyr Ser Val His Phe Tyr Thr Gly Ser His Glu Pro Ser Asp Thr
                260                 265                 270 agc tat cct gaa ggc act ccg tcc tcg gaa cgg aat aac gtt atg gca    960
Ser Tyr Pro Glu Gly Thr Pro Ser Ser Glu Arg Asn Asn Val Met Ala
            275                 280                 285 aat gta cga tat gca ctc gag aat ggt gct gca gtt ttt gct aca gaa   1008
Asn Val Arg Tyr Ala Leu Glu Asn Gly Ala Ala Val Phe Ala Thr Glu
            290                 295                 300 tgg ggt aca agc caa gcc aat ggt gat ggc ggc cca tac ctt gac gaa   1056
Trp Gly Thr Ser Gln Ala Asn Gly Asp Gly Gly Pro Tyr Leu Asp Glu
305                 310                 315 gct gat gta tgg ctt aac ttc ctt aac gag aac aat atc agc tgg gtc   1104
Ala Asp Val Trp Leu Asn Phe Leu Asn Glu Asn Asn Ile Ser Trp Val
320                 325                 330                 335 aac tgg tca ttg aca aat aaa aac gaa aca tca ggt tcc ttc act ccc   1152
Asn Trp Ser Leu Thr Asn Lys Asn Glu Thr Ser Gly Ser Phe Thr Pro
                340                 345                 350 ttt gag ctg ggg aaa tcc aat gcc aca agt ctt gat cct ggc cct gaa   1200
Phe Glu Leu Gly Lys Ser Asn Ala Thr Ser Leu Asp Pro Gly Pro Glu
            355                 360                 365 caa gca tgg tcc ctg ccg gaa cta agc gta tca ggc gag tat gtt cgt   1248
Gln Ala Trp Ser Leu Pro Glu Leu Ser Val Ser Gly Glu Tyr Val Arg
            370                 375                 380 tca cga att aaa ggt agt ccg tat gaa ccg ttt gac cgg acg aaa ttt   1296
Ser Arg Ile Lys Gly Ser Pro Tyr Glu Pro Phe Asp Arg Thr Lys Phe
385                 390                 395 aat aaa gta atc tgg gat ttt aac gac ggt aca gtt cag ggg ttt gaa   1344
Asn Lys Val Ile Trp Asp Phe Asn Asp Gly Thr Val Gln Gly Phe Glu
400                 405                 410                 415 gta aat gac gac agt cct gtt aaa gaa gaa ata gct gtc agc aat gca   1392
Val Asn Asp Asp Ser Pro Val Lys Glu Glu Ile Ala Val Ser Asn Ala
                420                 425                 430 ggt aat gcc ctt caa att acc ggt ctt aat gct agc aac gac atc tcc   1440
Gly Asn Ala Leu Gln Ile Thr Gly Leu Asn Ala Ser Asn Asp Ile Ser
            435                 440                 445 aca gat aac ttc tgg agt aac ctc agg ctt tca gcc aat tcc tgg gga   1488
Thr Asp Asn Phe Trp Ser Asn Leu Arg Leu Ser Ala Asn Ser Trp Gly
            450                 455                 460 gaa tcg gtt aat atc ctg ggg gca gaa gaa ctg aca tta gat gtg atc   1536
Glu Ser Val Asn Ile Leu Gly Ala Glu Glu Leu Thr Leu Asp Val Ile
465                 470                 475 gtc gat gag cca act tcc gtc tca atc gca gca att ccg caa agt gca   1584
Val Asp Glu Pro Thr Ser Val Ser Ile Ala Ala Ile Pro Gln Ser Ala
480                 485                 490                 495
```

| | | | | | | | | | | | | | | |
|---|---|---|---|---|---|---|---|---|---|---|---|---|---|---|
| gca | gtt | ggc | tgg | gca | aat | cct | aac | aat | gcg | gtc | gtt | gtt | tct | aaa gaa | 1632 |
| Ala | Val | Gly | Trp | Ala | Asn | Pro | Asn | Asn | Ala | Val | Val | Val | Ser | Lys Glu | |
| | | | 500 | | | | | 505 | | | | | 510 | | |
| gat | ttc | gca | cct | tat | ggt | ggc | cag | tat | aag | gct | gtc | ctg | acg | ata aca | 1680 |
| Asp | Phe | Ala | Pro | Tyr | Gly | Gly | Gln | Tyr | Lys | Ala | Val | Leu | Thr | Ile Thr | |
| | | 515 | | | | | 520 | | | | | 525 | | | |
| ccg | gaa | gat | tct | cca | gct | ctg | ggt | gcc | ata | gca | aca | cat | agt | gat gat | 1728 |
| Pro | Glu | Asp | Ser | Pro | Ala | Leu | Gly | Ala | Ile | Ala | Thr | His | Ser | Asp Asp | |
| | 530 | | | | | 535 | | | | | 540 | | | | |
| aac | atg | atg | aat | aac | att | atc | ttg | ttt | ata | ggt | aca | gaa | aat | gct gat | 1776 |
| Asn | Met | Met | Asn | Asn | Ile | Ile | Leu | Phe | Ile | Gly | Thr | Glu | Asn | Ala Asp | |
| | 545 | | | | | 550 | | | | | 555 | | | | |
| gta | ctc | tca | ctt | gat | aac | att | aca | gtt | aaa | ggt | tcc | atc | gtt | gaa att | 1824 |
| Val | Leu | Ser | Leu | Asp | Asn | Ile | Thr | Val | Lys | Gly | Ser | Ile | Val | Glu Ile | |
| 560 | | | | | 565 | | | | | 570 | | | | | 575 |
| cca | gta | atc | cat | gat | cca | aag | ggc | atc | gcg | gtt | ctt | cct | tca | aac ttt | 1872 |
| Pro | Val | Ile | His | Asp | Pro | Lys | Gly | Ile | Ala | Val | Leu | Pro | Ser | Asn Phe | |
| | | | 580 | | | | | 585 | | | | | 590 | | |
| gag | gac | gga | acc | cgc | caa | ggc | tgg | gac | tgg | aac | cct | gaa | tca | ggg gta | 1920 |
| Glu | Asp | Gly | Thr | Arg | Gln | Gly | Trp | Asp | Trp | Asn | Pro | Glu | Ser | Gly Val | |
| | | 595 | | | | | 600 | | | | | 605 | | | |
| aaa | act | gct | tta | aca | att | aaa | gag | gcc | gat | ggt | tca | cat | gcc | cta tcc | 1968 |
| Lys | Thr | Ala | Leu | Thr | Ile | Lys | Glu | Ala | Asp | Gly | Ser | His | Ala | Leu Ser | |
| | 610 | | | | | 615 | | | | | 620 | | | | |
| tgg | gag | ttt | gct | tac | ccg | gaa | gtt | aaa | cct | ggt | gat | ggg | tgg | gca aca | 2016 |
| Trp | Glu | Phe | Ala | Tyr | Pro | Glu | Val | Lys | Pro | Gly | Asp | Gly | Trp | Ala Thr | |
| | 625 | | | | | 630 | | | | | 635 | | | | |
| gct | cca | cga | ttg | gag | ttt | tgg | aaa | gat | gga | ctg | gta | aga | gga | gca aac | 2064 |
| Ala | Pro | Arg | Leu | Glu | Phe | Trp | Lys | Asp | Gly | Leu | Val | Arg | Gly | Ala Asn | |
| 640 | | | | | 645 | | | | | 650 | | | | | 655 |
| gat | tac | ctc | tca | ttt | gat | tta | tac | ctt | gac | cct | gtc | cgt | gcc | aca gag | 2112 |
| Asp | Tyr | Leu | Ser | Phe | Asp | Leu | Tyr | Leu | Asp | Pro | Val | Arg | Ala | Thr Glu | |
| | | | 660 | | | | | 665 | | | | | 670 | | |
| ggt | gct | atc | aca | aca | cat | ctc | gta | ttc | cag | ccg | cca | agt | gct | gga tac | 2160 |
| Gly | Ala | Ile | Thr | Thr | His | Leu | Val | Phe | Gln | Pro | Pro | Ser | Ala | Gly Tyr | |
| | | 675 | | | | | 680 | | | | | 685 | | | |
| tgg | gta | caa | gct | cca | gct | tct | cac | agc | ata | gat | ttg | tta | aac | tta gat | 2208 |
| Trp | Val | Gln | Ala | Pro | Ala | Ser | His | Ser | Ile | Asp | Leu | Leu | Asn | Leu Asp | |
| | 690 | | | | | 695 | | | | | 700 | | | | |
| tca | gct | gat | atc | aca | gca | gat | gga | ctg | tac | cat | tat | gaa | gtg | aaa ttc | 2256 |
| Ser | Ala | Asp | Ile | Thr | Ala | Asp | Gly | Leu | Tyr | His | Tyr | Glu | Val | Lys Phe | |
| 705 | | | | | 710 | | | | | 715 | | | | | |
| aat | att | aga | gac | att | aca | gca | att | caa | gat | gac | aca | gct | ctg | cgc aat | 2304 |
| Asn | Ile | Arg | Asp | Ile | Thr | Ala | Ile | Gln | Asp | Asp | Thr | Ala | Leu | Arg Asn | |
| 720 | | | | | 725 | | | | | 730 | | | | | 735 |
| atg | atc | ctc | ata | ttg | gag | gat | agg | aac | agc | gac | ttc | gcg | ggc | cgg gcg | 2352 |
| Met | Ile | Leu | Ile | Leu | Glu | Asp | Arg | Asn | Ser | Asp | Phe | Ala | Gly | Arg Ala | |
| | | | | 740 | | | | | 745 | | | | | 750 | |
| ttc | atc | gac | aat | gta | aga | ttc | gaa | taa | | | | | | | 2379 |
| Phe | Ile | Asp | Asn | Val | Arg | Phe | Glu | | | | | | | | |
| | | | | 755 | | | | | | | | | | | |

<210> SEQ ID NO 2
<211> LENGTH: 792
<212> TYPE: PRT
<213> ORGANISM: Bacillus sp. ACE160

<400> SEQUENCE: 2

Val Arg Gln Pro Ile Gly Lys Lys Ile Ile Ala Ala Gly Met Ile Phe
           -30                 -25                 -20

```
            Thr Leu Leu Phe Ser Leu Ile Val Thr Val Phe Pro Thr Ala Gly Gln
                -15                 -10                 -5

Ala Leu Glu Ser Asp Tyr Ser His Leu Leu Gly Asn Asp Ala Val Lys
            -1  1               5                   10                  15

Arg Pro Ser Glu Gly Gly Ala Leu Ser Leu Cys Asn Glu Thr Thr Pro
                            20                  25                  30

Val Lys Pro Asn His Ala Gly Asp Arg Gly Lys Pro Ser His Ala Gly
                        35                  40                  45

Lys Gly Lys Pro Pro His Ala Gly Lys Pro Glu His Ala Gly Pro Lys
                        50                  55                  60

Arg Lys Thr Leu Cys Asp Ala Thr Gly Ser Gln Ile Gln Leu Arg Gly
                65                  70                  75

Met Ser Thr His Gly Leu Gln Trp Phe Gly Glu Ile Ile Asn Asp Asn
            80                  85                  90                  95

Ala Phe Ala Ala Leu Ser Asn Asp Trp Glu Ala Asn Met Ile Arg Leu
                            100                 105                 110

Ala Met Tyr Ile Gly Glu Asn Gly Tyr Ala Thr Asn Pro Glu Val Lys
                            115                 120                 125

Glu Leu Val Tyr Glu Gly Ile Glu Leu Ala Phe Lys His Asp Met Tyr
                        130                 135                 140

Val Ile Val Asp Trp His Val His Ala Pro Gly Asp Pro Arg Ala Asp
                145                 150                 155

Ile Tyr Ser Gly Ala Leu Asp Phe Phe Lys Glu Ile Ala Asp His Tyr
            160                 165                 170                 175

Lys Asp His Pro Lys Phe His Tyr Ile Ile Trp Glu Ile Ala Asn Glu
                            180                 185                 190

Pro Ser Pro Asn Asn Ser Gly Gly Pro Gly Ile Pro Asn Asp Glu Thr
                            195                 200                 205

Gly Trp Lys Ala Val Lys Glu Tyr Ala Glu Pro Ile Val Glu Met Leu
                        210                 215                 220

Arg Glu Arg Gly Asp Asn Ile Ile Leu Val Gly Ser Pro Asn Trp Ser
                225                 230                 235

Gln Arg Pro Asp Leu Ala Ala Asp Asn Pro Ile Asp Ala Lys Asn Ile
            240                 245                 250                 255

Met Tyr Ser Val His Phe Tyr Thr Gly Ser His Glu Pro Ser Asp Thr
                            260                 265                 270

Ser Tyr Pro Glu Gly Thr Pro Ser Ser Glu Arg Asn Asn Val Met Ala
                            275                 280                 285

Asn Val Arg Tyr Ala Leu Glu Asn Gly Ala Ala Val Phe Ala Thr Glu
                        290                 295                 300

Trp Gly Thr Ser Gln Ala Asn Gly Asp Gly Gly Pro Tyr Leu Asp Glu
                305                 310                 315

Ala Asp Val Trp Leu Asn Phe Leu Asn Glu Asn Asn Ile Ser Trp Val
            320                 325                 330                 335

Asn Trp Ser Leu Thr Asn Lys Asn Glu Thr Ser Gly Ser Phe Thr Pro
                            340                 345                 350

Phe Glu Leu Gly Lys Ser Asn Ala Thr Ser Leu Asp Pro Gly Pro Glu
                            355                 360                 365

Gln Ala Trp Ser Leu Pro Glu Leu Ser Val Ser Gly Glu Tyr Val Arg
                        370                 375                 380

Ser Arg Ile Lys Gly Ser Pro Tyr Glu Pro Phe Asp Arg Thr Lys Phe
                385                 390                 395

Asn Lys Val Ile Trp Asp Phe Asn Asp Gly Thr Val Gln Gly Phe Glu
            400                 405                 410                 415
```

```
Val Asn Asp Asp Ser Pro Val Lys Glu Glu Ile Ala Val Ser Asn Ala
            420                 425                 430

Gly Asn Ala Leu Gln Ile Thr Gly Leu Asn Ala Ser Asn Asp Ile Ser
        435                 440                 445

Thr Asp Asn Phe Trp Ser Asn Leu Arg Leu Ser Ala Asn Ser Trp Gly
    450                 455                 460

Glu Ser Val Asn Ile Leu Gly Ala Glu Leu Thr Leu Asp Val Ile
465                 470                 475

Val Asp Glu Pro Thr Ser Val Ser Ile Ala Ala Ile Pro Gln Ser Ala
480                 485                 490                 495

Ala Val Gly Trp Ala Asn Pro Asn Asn Ala Val Val Ser Lys Glu
                500                 505                 510

Asp Phe Ala Pro Tyr Gly Gly Gln Tyr Lys Ala Val Leu Thr Ile Thr
            515                 520                 525

Pro Glu Asp Ser Pro Ala Leu Gly Ala Ile Ala Thr His Ser Asp Asp
            530                 535                 540

Asn Met Met Asn Asn Ile Ile Leu Phe Ile Gly Thr Glu Asn Ala Asp
        545                 550                 555

Val Leu Ser Leu Asp Asn Ile Thr Val Lys Gly Ser Ile Val Glu Ile
560                 565                 570                 575

Pro Val Ile His Asp Pro Lys Gly Ile Ala Val Leu Pro Ser Asn Phe
            580                 585                 590

Glu Asp Gly Thr Arg Gln Gly Trp Asp Trp Asn Pro Glu Ser Gly Val
            595                 600                 605

Lys Thr Ala Leu Thr Ile Lys Glu Ala Asp Gly Ser His Ala Leu Ser
        610                 615                 620

Trp Glu Phe Ala Tyr Pro Glu Val Lys Pro Gly Asp Gly Trp Ala Thr
    625                 630                 635

Ala Pro Arg Leu Glu Phe Trp Lys Asp Gly Leu Val Arg Gly Ala Asn
640                 645                 650                 655

Asp Tyr Leu Ser Phe Asp Leu Tyr Leu Asp Pro Val Arg Ala Thr Glu
            660                 665                 670

Gly Ala Ile Thr Thr His Leu Val Phe Gln Pro Pro Ser Ala Gly Tyr
            675                 680                 685

Trp Val Gln Ala Pro Ala Ser His Ser Ile Asp Leu Leu Asn Leu Asp
        690                 695                 700

Ser Ala Asp Ile Thr Ala Asp Gly Leu Tyr His Tyr Glu Val Lys Phe
705                 710                 715

Asn Ile Arg Asp Ile Thr Ala Ile Gln Asp Asp Thr Ala Leu Arg Asn
720                 725                 730                 735

Met Ile Leu Ile Leu Glu Asp Arg Asn Ser Asp Phe Ala Gly Arg Ala
            740                 745                 750

Phe Ile Asp Asn Val Arg Phe Glu
            755

<210> SEQ ID NO 3
<211> LENGTH: 32
<212> TYPE: DNA
<213> ORGANISM: Artificial sequence
<220> FEATURE:
<223> OTHER INFORMATION: Primer

<400> SEQUENCE: 3
gattaacgcg ttcctcgtgc tgagcacaga gg                              32
```

```
<210> SEQ ID NO 4
<211> LENGTH: 31
<212> TYPE: DNA
<213> ORGANISM: Artificial sequence
<220> FEATURE:
<223> OTHER INFORMATION: Primer

<400> SEQUENCE: 4
ttatggagct caaatcaact ctaggaggct g                              31

<210> SEQ ID NO 5
<211> LENGTH: 822
<212> TYPE: PRT
<213> ORGANISM: Unknown
<220> FEATURE:
<223> OTHER INFORMATION: Bacillus species

<400> SEQUENCE: 5

Met Met Leu Arg Lys Lys Thr Lys Gln Leu Ile Ser Ser Ile Leu Ile
1               5                   10                  15

Leu Val Leu Leu Leu Ser Leu Phe Pro Thr Ala Leu Ala Ala Glu Gly
            20                  25                  30

Asn Thr Arg Glu Asp Asn Phe Lys His Leu Leu Gly Asn Asp Asn Val
        35                  40                  45

Lys Arg Pro Ser Glu Ala Gly Ala Leu Gln Leu Gln Glu Val Asp Gly
    50                  55                  60

Gln Met Thr Leu Val Asp Gln His Gly Glu Lys Ile Gln Leu Arg Gly
65                  70                  75                  80

Met Ser Thr His Gly Leu Gln Trp Phe Pro Glu Ile Leu Asn Asp Asn
                85                  90                  95

Ala Tyr Lys Ala Leu Ala Asn Asp Trp Glu Ser Asn Met Ile Arg Leu
            100                 105                 110

Ala Met Tyr Val Gly Glu Asn Gly Tyr Ala Ser Asn Pro Glu Leu Ile
        115                 120                 125

Lys Ser Arg Val Ile Lys Gly Ile Asp Leu Ala Ile Glu Asn Asp Met
    130                 135                 140

Tyr Val Ile Val Asp Trp His Val His Ala Pro Gly Asp Pro Arg Asp
145                 150                 155                 160

Pro Val Tyr Ala Gly Ala Glu Asp Phe Phe Arg Asp Ile Ala Ala Leu
                165                 170                 175

Tyr Pro Asn Asn Pro His Ile Ile Tyr Glu Leu Ala Asn Glu Pro Ser
            180                 185                 190

Ser Asn Asn Asn Gly Gly Ala Gly Ile Pro Asn Asn Glu Glu Gly Trp
        195                 200                 205

Asn Ala Val Lys Glu Tyr Ala Asp Pro Ile Val Glu Met Leu Arg Asp
    210                 215                 220

Ser Gly Asn Ala Asp Asp Asn Ile Ile Ile Val Gly Ser Pro Asn Trp
225                 230                 235                 240

Ser Gln Arg Pro Asp Leu Ala Ala Asp Asn Pro Ile Asp Asp His His
                245                 250                 255

Thr Met Tyr Thr Val His Phe Tyr Thr Gly Ser His Ala Ala Ser Thr
            260                 265                 270

Glu Ser Tyr Pro Pro Glu Thr Pro Asn Ser Glu Arg Gly Asn Val Met
        275                 280                 285

Ser Asn Thr Arg Tyr Ala Leu Glu Asn Gly Val Ala Val Phe Ala Thr
    290                 295                 300

Glu Trp Gly Thr Ser Gln Ala Asn Gly Asp Gly Gly Pro Tyr Phe Asp
305                 310                 315                 320
```

```
Glu Ala Asp Val Trp Ile Glu Phe Leu Asn Glu Asn Ile Ser Trp
            325                 330                 335

Ala Asn Trp Ser Leu Thr Asn Lys Asn Glu Val Ser Gly Ala Phe Thr
            340                 345                 350

Pro Phe Glu Leu Gly Lys Ser Asn Ala Thr Ser Leu Asp Pro Gly Pro
            355                 360                 365

Asp Gln Val Trp Val Pro Glu Glu Leu Ser Leu Ser Gly Glu Tyr Val
            370                 375                 380

Arg Ala Arg Ile Lys Gly Val Asn Tyr Glu Pro Ile Asp Arg Thr Lys
385                 390                 395                 400

Tyr Thr Lys Val Leu Trp Asp Phe Asn Asp Gly Thr Lys Gln Gly Phe
                405                 410                 415

Gly Val Asn Gly Asp Ser Pro Val Glu Asp Val Val Ile Glu Asn Glu
            420                 425                 430

Ala Gly Ala Leu Lys Leu Ser Gly Leu Asp Ala Ser Asn Asp Val Ser
            435                 440                 445

Glu Gly Asn Tyr Trp Ala Asn Ala Arg Leu Ser Ala Asp Gly Trp Gly
            450                 455                 460

Lys Ser Val Asp Ile Leu Gly Ala Glu Lys Leu Thr Met Asp Val Ile
465                 470                 475                 480

Val Asp Glu Pro Thr Thr Val Ser Ile Ala Ala Ile Pro Gln Gly Pro
                485                 490                 495

Ser Ala Asn Trp Val Asn Pro Asn Arg Ala Ile Lys Val Glu Pro Thr
            500                 505                 510

Asn Phe Val Pro Leu Gly Asp Lys Phe Lys Ala Glu Leu Thr Ile Thr
            515                 520                 525

Ser Ala Asp Ser Pro Ser Leu Glu Ala Ile Ala Met His Ala Glu Asn
            530                 535                 540

Asn Asn Ile Asn Asn Ile Ile Leu Phe Val Gly Thr Glu Gly Ala Asp
545                 550                 555                 560

Val Ile Tyr Leu Asp Asn Ile Lys Val Ile Gly Thr Glu Val Glu Ile
                565                 570                 575

Pro Val Val His Asp Pro Lys Gly Glu Ala Val Leu Pro Ser Val Phe
            580                 585                 590

Glu Asp Gly Thr Arg Gln Gly Trp Asp Trp Ala Gly Glu Ser Gly Val
            595                 600                 605

Lys Thr Ala Leu Thr Ile Glu Glu Ala Asn Gly Ser Asn Ala Leu Ser
610                 615                 620

Trp Glu Phe Gly Tyr Pro Glu Val Lys Pro Ser Asp Asn Trp Ala Thr
625                 630                 635                 640

Ala Pro Arg Leu Asp Phe Trp Lys Ser Asp Leu Val Arg Gly Glu Asn
                645                 650                 655

Asp Tyr Val Thr Phe Asp Phe Tyr Leu Asp Pro Val Arg Ala Thr Glu
            660                 665                 670

Gly Ala Met Asn Ile Asn Leu Val Phe Gln Pro Pro Thr Asn Gly Tyr
            675                 680                 685

Trp Val Gln Ala Pro Lys Thr Tyr Thr Ile Asn Phe Asp Glu Leu Glu
            690                 695                 700

Glu Ala Asn Gln Val Asn Gly Leu Tyr His Tyr Glu Val Lys Ile Asn
705                 710                 715                 720

Val Arg Asp Ile Thr Asn Ile Gln Asp Asp Thr Leu Leu Arg Asn Met
                725                 730                 735

Met Ile Ile Phe Ala Asp Val Glu Ser Asp Phe Ala Gly Arg Val Phe
```

```
            740                 745                 750
Val Asp Asn Val Arg Phe Glu Gly Ala Ala Thr Thr Glu Pro Val Glu
            755                 760                 765

Pro Glu Pro Val Asp Pro Gly Glu Thr Pro Pro Val Asp Glu Lys
        770                 775                 780

Glu Ala Lys Lys Glu Gln Lys Glu Ala Glu Lys Glu Lys Glu Ala
785                 790                 795                 800

Val Lys Glu Glu Lys Glu Ala Lys Glu Lys Lys Ala Ile Lys
            805                 810                 815

Asn Glu Ala Thr Lys Lys
            820

<210> SEQ ID NO 6
<211> LENGTH: 941
<212> TYPE: PRT
<213> ORGANISM: Unknown
<220> FEATURE:
<223> OTHER INFORMATION: Bacillus species

<400> SEQUENCE: 6

Met Lys Ile Lys Gln Ile Lys Gln Ser Leu Ser Leu Leu Ile Ile
1               5                   10                  15

Thr Leu Ile Met Ser Leu Phe Val Pro Met Ala Ser Ala Asn Thr Asn
            20                  25                  30

Glu Ser Lys Ser Asn Ala Phe Pro Phe Ser Asp Val Lys Lys Thr Ser
        35                  40                  45

Trp Ser Phe Pro Tyr Ile Lys Asp Leu Tyr Gln Glu Val Ile Thr
50                  55                  60

Gly Thr Ser Ala Thr Thr Phe Ser Pro Thr Asp Ser Val Thr Arg Ala
65                  70                  75                  80

Gln Phe Thr Val Met Leu Thr Arg Gly Leu Gly Leu Glu Ala Ser Ser
            85                  90                  95

Lys Asp Tyr Pro Phe Lys Asp Arg Lys Asn Trp Ala Tyr Lys Glu Ile
        100                 105                 110

Gln Ala Ala Tyr Glu Ala Gly Ile Val Thr Gly Lys Thr Asn Gly Glu
            115                 120                 125

Phe Ala Pro Asn Glu Asn Ile Thr Arg Glu Gln Met Ala Ala Met Ala
        130                 135                 140

Val Arg Ala Tyr Glu Tyr Leu Glu Asn Glu Leu Ser Leu Pro Glu Glu
145                 150                 155                 160

Gln Arg Glu Tyr Asn Asp Ser Ser Ser Ile Ser Thr Phe Ala Gln Asp
            165                 170                 175

Ala Val Gln Lys Ala Tyr Val Leu Glu Leu Met Glu Gly Asn Thr Asp
        180                 185                 190

Gly Tyr Phe Gln Pro Lys Arg Asn Ser Thr Arg Glu Gln Ser Ala Lys
            195                 200                 205

Val Ile Ser Thr Leu Leu Trp Lys Val Ala Ser His Asp Tyr Leu Tyr
        210                 215                 220

His Thr Glu Ala Val Lys Ser Pro Ser Glu Ala Gly Ala Leu Gln Leu
225                 230                 235                 240

Val Glu Leu Asn Gly Gln Leu Thr Leu Ala Gly Glu Asp Gly Thr Pro
            245                 250                 255

Val Gln Leu Arg Gly Met Ser Thr His Gly Leu Gln Trp Phe Gly Glu
        260                 265                 270

Ile Val Asn Glu Asn Ala Phe Val Ala Leu Ser Asn Asp Trp Gly Ser
            275                 280                 285
```

-continued

```
Asn Met Ile Arg Leu Ala Met Tyr Ile Gly Glu Asn Gly Tyr Ala Thr
    290                 295                 300

Asn Pro Glu Val Lys Asp Leu Val Tyr Glu Gly Ile Glu Leu Ala Phe
305                 310                 315                 320

Glu His Asp Met Tyr Val Ile Val Asp Trp His Val His Ala Pro Gly
                325                 330                 335

Asp Pro Arg Ala Asp Val Tyr Ser Gly Ala Tyr Asp Phe Phe Glu Glu
            340                 345                 350

Ile Ala Asp His Tyr Lys Asp His Pro Lys Asn His Tyr Ile Ile Trp
        355                 360                 365

Glu Leu Ala Asn Glu Pro Ser Pro Asn Asn Asn Gly Gly Pro Gly Leu
    370                 375                 380

Thr Asn Asp Glu Lys Gly Trp Glu Ala Val Lys Glu Tyr Ala Glu Pro
385                 390                 395                 400

Ile Val Glu Met Leu Arg Glu Lys Gly Asp Asn Met Ile Leu Val Gly
                405                 410                 415

Asn Pro Asn Trp Ser Gln Arg Pro Asp Leu Ser Ala Asp Asn Pro Ile
            420                 425                 430

Asp Ala Glu Asn Ile Met Tyr Ser Val His Phe Tyr Thr Gly Ser His
        435                 440                 445

Gly Ala Ser His Ile Gly Tyr Pro Glu Gly Thr Pro Ser Ser Glu Arg
    450                 455                 460

Ser Asn Val Met Ala Asn Val Arg Tyr Ala Leu Asp Asn Gly Val Ala
465                 470                 475                 480

Val Phe Ala Thr Glu Trp Gly Thr Ser Gln Ala Asn Gly Asp Gly Gly
                485                 490                 495

Pro Tyr Phe Asp Glu Ala Asp Val Trp Leu Asn Phe Leu Asn Lys His
            500                 505                 510

Asn Ile Ser Trp Ala Asn Trp Ser Leu Thr Asn Lys Asn Glu Ile Ser
        515                 520                 525

Gly Ala Phe Thr Pro Phe Glu Leu Gly Arg Thr Asp Ala Thr Asp Leu
    530                 535                 540

Asp Pro Gly Ala Asn Gln Val Trp Ala Pro Glu Glu Leu Ser Leu Ser
545                 550                 555                 560

Gly Glu Tyr Val Arg Ala Arg Ile Lys Gly Ile Glu Tyr Thr Pro Ile
                565                 570                 575

Asp Arg Thr Lys Phe Thr Lys Leu Val Trp Asp Phe Asn Asp Gly Thr
            580                 585                 590

Thr Gln Gly Phe Gln Val Asn Gly Asp Ser Pro Asn Lys Glu Ser Ile
        595                 600                 605

Thr Leu Ser Asn Asn Asn Asp Ala Leu Gln Ile Glu Gly Leu Asn Val
    610                 615                 620

Ser Asn Asp Ile Ser Glu Gly Asn Tyr Trp Asp Asn Val Arg Leu Ser
625                 630                 635                 640

Ala Asp Gly Trp Ser Glu Asn Val Asp Ile Leu Gly Ala Thr Glu Leu
                645                 650                 655

Thr Ile Asp Val Ile Val Glu Glu Pro Thr Thr Val Ser Ile Ala Ala
            660                 665                 670

Ile Pro Gln Gly Pro Ala Gly Trp Ala Asn Pro Thr Arg Ala Ile
        675                 680                 685

Lys Val Thr Glu Asp Asp Phe Glu Ser Phe Gly Asp Gly Tyr Lys Ala
    690                 695                 700

Leu Val Thr Ile Thr Ser Glu Asp Ser Pro Ser Leu Glu Thr Ile Ala
```

```
                705                 710                 715                 720
Thr Ser Pro Glu Asp Asn Thr Met Ser Asn Ile Ile Leu Phe Val Gly
                    725                 730                 735

Thr Glu Asp Ala Asp Val Ile Ser Leu Asp Asn Ile Thr Val Ser Gly
                740                 745                 750

Thr Glu Ile Glu Ile Glu Val Ile His Asp Glu Lys Gly Thr Ala Thr
            755                 760                 765

Leu Pro Ser Thr Phe Glu Asp Gly Thr Arg Gln Gly Trp Asp Trp His
    770                 775                 780

Thr Glu Ser Gly Val Lys Thr Ala Leu Thr Ile Glu Glu Ala Asn Gly
785                 790                 795                 800

Ser Asn Ala Leu Ser Trp Glu Tyr Ala Tyr Pro Glu Val Lys Pro Ser
                805                 810                 815

Asp Gly Trp Ala Thr Ala Pro Arg Leu Asp Phe Trp Lys Asp Glu Leu
                820                 825                 830

Val Arg Gly Thr Ser Asp Tyr Ile Ser Phe Asp Phe Tyr Ile Asp Ala
            835                 840                 845

Val Arg Ala Ser Glu Gly Ala Ile Ser Ile Asn Ala Val Phe Gln Pro
    850                 855                 860

Pro Ala Asn Gly Tyr Trp Gln Glu Val Pro Thr Thr Phe Glu Ile Asp
865                 870                 875                 880

Leu Thr Glu Leu Asp Ser Ala Thr Val Thr Ser Asp Glu Leu Tyr His
                885                 890                 895

Tyr Glu Val Lys Ile Asn Ile Arg Asp Ile Glu Ala Ile Thr Asp Asp
                900                 905                 910

Thr Glu Leu Arg Asn Leu Leu Leu Ile Phe Ala Asp Glu Asp Ser Asp
            915                 920                 925

Phe Ala Gly Arg Val Phe Val Asp Asn Val Arg Phe Glu
    930                 935                 940

<210> SEQ ID NO 7
<211> LENGTH: 941
<212> TYPE: PRT
<213> ORGANISM: Unknown
<220> FEATURE:
<223> OTHER INFORMATION: Bacillus species

<400> SEQUENCE: 7

Met Lys Ile Lys Gln Ile Lys Gln Ser Leu Ser Leu Leu Ile Ile
1               5                   10                  15

Thr Leu Ile Met Ser Leu Phe Val Pro Met Ala Ser Ala Asn Thr Asn
                20                  25                  30

Glu Ser Lys Ser Asn Ala Phe Pro Phe Ser Asp Val Lys Lys Thr Ser
            35                  40                  45

Trp Ser Phe Pro Tyr Ile Lys Asp Leu Tyr Glu Gln Glu Val Ile Thr
    50                  55                  60

Gly Thr Ser Ala Thr Thr Phe Ser Pro Thr Asp Ser Val Thr Arg Ala
65                  70                  75                  80

Gln Phe Thr Val Met Leu Thr Arg Gly Leu Gly Leu Glu Ala Ser Ser
                85                  90                  95

Lys Asp Tyr Pro Phe Lys Asp Arg Lys Asn Trp Ala Tyr Lys Glu Ile
            100                 105                 110

Gln Ala Ala Tyr Glu Ala Gly Ile Val Thr Gly Lys Thr Asn Gly Glu
    115                 120                 125

Phe Ala Pro Asn Glu Asn Ile Thr Arg Glu Gln Met Ala Ala Met Ala
130                 135                 140
```

```
Val Arg Ala Tyr Glu Tyr Leu Glu Asn Glu Leu Ser Leu Pro Glu Glu
145                 150                 155                 160

Gln Arg Glu Tyr Asn Asp Ser Ser Ile Ser Thr Phe Ala Gln Asp
                165                 170                 175

Ala Val Gln Lys Ala Tyr Val Leu Glu Leu Met Glu Gly Asn Thr Asp
                180                 185                 190

Gly Tyr Phe Gln Pro Lys Arg Asn Ser Thr Arg Glu Gln Ser Ala Lys
            195                 200                 205

Val Ile Ser Thr Leu Leu Trp Lys Val Ala Ser His Asp Tyr Leu Tyr
            210                 215                 220

His Thr Glu Ala Val Lys Ser Pro Ser Glu Ala Gly Ala Leu Gln Leu
225                 230                 235                 240

Val Glu Leu Asn Gly Gln Leu Thr Leu Ala Gly Glu Asp Gly Thr Pro
                245                 250                 255

Val Gln Leu Arg Gly Met Ser Thr His Gly Leu Gln Trp Phe Gly Glu
                260                 265                 270

Ile Val Asn Glu Asn Ala Phe Val Ala Leu Ser Asn Asp Trp Gly Ser
            275                 280                 285

Asn Met Ile Arg Leu Ala Met Tyr Ile Gly Glu Asn Gly Tyr Ala Thr
290                 295                 300

Asn Pro Glu Val Lys Asp Leu Val Tyr Glu Gly Ile Glu Leu Ala Phe
305                 310                 315                 320

Glu His Asp Met Tyr Val Ile Asp Trp His Val His Ala Pro Gly
                325                 330                 335

Asp Pro Arg Ala Asp Val Tyr Ser Gly Ala Tyr Asp Phe Phe Glu Glu
                340                 345                 350

Ile Ala Asp His Tyr Lys Asp His Pro Lys Asn His Tyr Ile Ile Trp
            355                 360                 365

Glu Leu Ala Asn Glu Pro Ser Pro Asn Asn Gly Gly Pro Gly Leu
            370                 375                 380

Thr Asn Asp Glu Lys Gly Trp Glu Ala Val Lys Glu Tyr Ala Glu Pro
385                 390                 395                 400

Ile Val Glu Met Leu Arg Glu Lys Gly Asp Asn Met Ile Leu Val Gly
                405                 410                 415

Asn Pro Asn Trp Ser Gln Arg Pro Asp Leu Ser Ala Asp Asn Pro Ile
                420                 425                 430

Asp Ala Glu Asn Ile Met Tyr Ser Val His Phe Tyr Thr Gly Ser His
            435                 440                 445

Gly Ala Ser His Ile Gly Tyr Pro Glu Gly Thr Pro Ser Ser Glu Arg
450                 455                 460

Ser Asn Val Met Ala Asn Val Val Leu Leu Leu Asp Asn Gly Val Ala
465                 470                 475                 480

Val Phe Ala Thr Glu Trp Gly Thr Ser Gln Ala Asn Gly Asp Gly Gly
                485                 490                 495

Pro Tyr Phe Asp Glu Ala Asp Val Trp Leu Asn Phe Leu Asn Lys His
                500                 505                 510

Asn Ile Ser Trp Ala Asn Trp Ser Leu Thr Asn Lys Asn Glu Ile Ser
            515                 520                 525

Gly Ala Phe Thr Pro Phe Glu Leu Gly Arg Thr Asp Ala Thr Asp Leu
            530                 535                 540

Asp Pro Gly Ala Asn Gln Val Trp Ala Pro Glu Glu Leu Ser Leu Ser
545                 550                 555                 560

Gly Glu Tyr Val Arg Ala Arg Ile Lys Gly Ile Glu Tyr Thr Pro Ile
```

565                 570                 575
Asp Arg Thr Lys Phe Thr Lys Leu Val Trp Asp Phe Asn Asp Gly Thr
            580                 585                 590

Thr Gln Gly Phe Gln Val Asn Gly Asp Ser Pro Asn Lys Glu Ser Ile
        595                 600                 605

Thr Leu Ser Asn Asn Asp Ala Leu Gln Ile Glu Gly Leu Asn Val
    610                 615                 620

Ser Asn Asp Ile Ser Glu Gly Asn Tyr Trp Asp Asn Val Arg Leu Ser
625                 630                 635                 640

Ala Asp Gly Trp Ser Glu Asn Val Asp Ile Leu Gly Ala Thr Glu Leu
                645                 650                 655

Thr Ile Asp Val Ile Val Glu Glu Pro Thr Thr Val Ser Ile Ala Ala
            660                 665                 670

Ile Pro Gln Gly Pro Ala Ala Gly Trp Ala Asn Pro Thr Arg Ala Ile
        675                 680                 685

Lys Val Thr Glu Asp Asp Phe Glu Ser Phe Gly Asp Gly Tyr Lys Ala
    690                 695                 700

Leu Val Thr Ile Thr Ser Glu Asp Ser Pro Ser Leu Glu Thr Ile Ala
705                 710                 715                 720

Thr Ser Pro Glu Asp Asn Thr Met Ser Asn Ile Ile Leu Phe Val Gly
                725                 730                 735

Thr Glu Asp Ala Asp Val Ile Ser Leu Asp Asn Ile Thr Val Ser Gly
            740                 745                 750

Thr Glu Ile Glu Ile Glu Val Ile His Asp Lys Gly Thr Ala Thr
        755                 760                 765

Leu Pro Ser Thr Phe Glu Asp Gly Thr Arg Gln Gly Trp Asp Trp His
    770                 775                 780

Thr Glu Ser Gly Val Lys Thr Ala Leu Thr Ile Glu Glu Ala Asn Gly
785                 790                 795                 800

Ser Asn Ala Leu Ser Trp Glu Tyr Ala Tyr Pro Glu Val Lys Pro Ser
                805                 810                 815

Asp Gly Trp Ala Thr Ala Pro Arg Leu Asp Phe Trp Lys Asp Glu Leu
            820                 825                 830

Val Arg Gly Thr Ser Asp Tyr Ile Ser Phe Asp Phe Tyr Ile Asp Ala
        835                 840                 845

Val Arg Ala Ser Glu Gly Ala Ile Ser Ile Asn Ala Val Phe Gln Pro
    850                 855                 860

Pro Ala Asn Gly Tyr Trp Gln Glu Val Pro Thr Thr Phe Glu Ile Asp
865                 870                 875                 880

Leu Thr Glu Leu Asp Ser Ala Thr Val Thr Ser Asp Glu Leu Tyr His
                885                 890                 895

Tyr Glu Val Lys Ile Asn Ile Arg Asp Ile Glu Ala Ile Thr Asp Asp
            900                 905                 910

Thr Glu Leu Arg Asn Leu Leu Leu Ile Phe Ala Asp Glu Asp Ser Asp
        915                 920                 925

Phe Ala Gly Arg Val Phe Val Asp Asn Val Arg Phe Glu
    930                 935                 940

<210> SEQ ID NO 8
<211> LENGTH: 824
<212> TYPE: PRT
<213> ORGANISM: Unknown
<220> FEATURE:
<223> OTHER INFORMATION: Bacillus species

<400> SEQUENCE: 8

```
Met Met Leu Arg Lys Lys Thr Lys Gln Leu Ile Ser Ser Ile Leu Ile
1               5                   10                  15

Leu Val Leu Leu Leu Ser Leu Phe Pro Ala Ala Leu Ala Ala Glu Gly
            20                  25                  30

Asn Thr Arg Glu Asp Asn Phe Lys His Leu Leu Gly Asn Asp Asn Val
        35                  40                  45

Lys Arg Pro Ser Glu Ala Gly Ala Leu Gln Leu Gln Glu Val Asp Gly
    50                  55                  60

Gln Met Thr Leu Val Asp Gln His Gly Glu Lys Ile Gln Leu Arg Gly
65                  70                  75                  80

Met Ser Thr His Gly Leu Gln Trp Phe Pro Glu Ile Leu Asn Asp Asn
                85                  90                  95

Ala Tyr Lys Ala Leu Ser Asn Asp Trp Asp Ser Asn Met Ile Arg Leu
        100                 105                 110

Ala Met Tyr Val Gly Glu Asn Gly Tyr Ala Thr Asn Pro Glu Leu Ile
        115                 120                 125

Lys Gln Arg Val Ile Asp Gly Ile Glu Leu Ala Ile Glu Asn Asp Met
    130                 135                 140

Tyr Val Ile Val Asp Trp His Val His Ala Pro Gly Asp Pro Arg Asp
145                 150                 155                 160

Pro Val Tyr Ala Gly Ala Lys Asp Phe Phe Arg Glu Ile Ala Ala Leu
                165                 170                 175

Tyr Pro Asn Asn Pro His Ile Ile Tyr Glu Leu Ala Asn Glu Pro Ser
        180                 185                 190

Ser Asn Asn Asn Gly Gly Ala Gly Ile Pro Asn Asn Glu Glu Gly Trp
    195                 200                 205

Lys Ala Val Lys Glu Tyr Ala Asp Pro Ile Val Glu Met Leu Arg Lys
        210                 215                 220

Ser Gly Asn Ala Asp Asp Asn Ile Ile Ile Val Gly Ser Pro Asn Trp
225                 230                 235                 240

Ser Gln Arg Pro Asp Leu Ala Ala Asp Asn Pro Ile Asp Asp His His
                245                 250                 255

Thr Met Tyr Thr Val His Phe Tyr Thr Gly Ser His Ala Ala Ser Thr
        260                 265                 270

Glu Ser Tyr Pro Ser Glu Thr Pro Asn Ser Glu Arg Gly Asn Val Met
    275                 280                 285

Ser Asn Thr Arg Tyr Ala Leu Glu Asn Gly Val Ala Val Phe Ala Thr
290                 295                 300

Glu Trp Gly Thr Ser Gln Ala Ser Gly Asp Gly Gly Pro Tyr Phe Asp
305                 310                 315                 320

Glu Ala Asp Val Trp Ile Glu Phe Leu Asn Glu Asn Asn Ile Ser Trp
                325                 330                 335

Ala Asn Trp Ser Leu Thr Asn Lys Asn Glu Val Ser Gly Ala Phe Thr
        340                 345                 350

Pro Phe Glu Leu Gly Lys Ser Asn Ala Thr Asn Leu Asp Pro Gly Pro
    355                 360                 365

Asp His Val Trp Ala Pro Glu Glu Leu Ser Leu Ser Gly Glu Tyr Val
    370                 375                 380

Arg Ala Arg Ile Lys Gly Val Asn Tyr Glu Pro Ile Asp Arg Thr Lys
385                 390                 395                 400

Tyr Thr Lys Val Leu Trp Asp Phe Asn Asp Gly Thr Lys Gln Gly Phe
                405                 410                 415

Gly Val Asn Ser Asp Ser Pro Asn Lys Glu Leu Ile Ala Val Asp Asn
```

```
                    420             425             430
Glu Asn Asn Thr Leu Lys Val Ser Gly Leu Asp Val Ser Asn Asp Val
                435             440             445

Ser Asp Gly Asn Phe Trp Ala Asn Ala Arg Leu Ser Ala Asn Gly Trp
450             455             460

Gly Lys Ser Val Asp Ile Leu Gly Ala Glu Lys Leu Thr Met Asp Val
465             470             475             480

Ile Val Asp Glu Pro Thr Thr Val Ala Ile Ala Ile Pro Gln Ser
                485             490             495

Ser Lys Ser Gly Trp Ala Asn Pro Glu Arg Ala Val Arg Val Asn Ala
            500             505             510

Glu Asp Phe Val Gln Gln Thr Asp Gly Lys Tyr Lys Ala Gly Leu Thr
        515             520             525

Ile Thr Gly Glu Asp Ala Pro Asn Leu Lys Asn Ile Ala Phe His Glu
    530             535             540

Glu Asp Asn Asn Met Asn Asn Ile Ile Leu Phe Val Gly Thr Asp Ala
545             550             555             560

Ala Asp Val Ile Tyr Leu Asp Asn Ile Lys Val Ile Gly Thr Glu Val
                565             570             575

Glu Ile Pro Val Val His Asp Pro Lys Gly Glu Ala Val Leu Pro Ser
            580             585             590

Val Phe Glu Asp Gly Thr Arg Gln Gly Trp Asp Trp Ala Gly Glu Ser
        595             600             605

Gly Val Lys Thr Ala Leu Thr Ile Glu Ala Asn Gly Ser Asn Ala
    610             615             620

Leu Ser Trp Glu Phe Gly Tyr Pro Glu Val Lys Pro Ser Asp Asn Trp
625             630             635             640

Ala Thr Ala Pro Arg Leu Asp Phe Trp Lys Ser Asp Leu Val Arg Gly
                645             650             655

Glu Asn Asp Tyr Val Ala Phe Asp Phe Tyr Leu Asp Pro Val Arg Ala
            660             665             670

Thr Glu Gly Ala Met Asn Ile Asn Leu Val Phe Gln Pro Pro Thr Asn
        675             680             685

Gly Tyr Trp Val Gln Ala Pro Lys Thr Tyr Thr Ile Asn Phe Asp Glu
    690             695             700

Leu Glu Glu Ala Asn Gln Val Asn Gly Leu Tyr His Tyr Glu Val Lys
705             710             715             720

Ile Asn Val Arg Asp Ile Thr Asn Ile Gln Asp Asp Thr Leu Leu Arg
                725             730             735

Asn Met Met Ile Ile Phe Ala Asp Val Glu Ser Asp Phe Ala Gly Arg
            740             745             750

Val Phe Val Asp Asn Val Arg Phe Glu Gly Ala Ala Thr Thr Glu Pro
        755             760             765

Val Glu Pro Glu Pro Val Asp Pro Gly Glu Glu Thr Pro Pro Val Asp
    770             775             780

Glu Lys Glu Ala Lys Lys Glu Gln Lys Glu Ala Glu Lys Glu Lys
785             790             795             800

Glu Ala Val Lys Glu Glu Lys Lys Glu Ala Lys Glu Glu Lys Lys Ala
                805             810             815

Val Lys Asn Glu Ala Lys Lys Lys
            820

<210> SEQ ID NO 9
<211> LENGTH: 773
```

```
<212> TYPE: PRT
<213> ORGANISM: Unknown
<220> FEATURE:
<223> OTHER INFORMATION: Bacillus species

<400> SEQUENCE: 9

Ala Glu Gly Asn Thr Arg Glu Asp Asn Phe Lys His Leu Leu Gly Asn
1               5                   10                  15

Asp Asn Val Lys Arg Pro Ser Glu Ala Gly Leu Gln Leu Gln Glu
            20                  25                  30

Val Asp Gly Gln Met Thr Leu Val Asp Gln His Gly Glu Lys Ile Gln
        35                  40                  45

Leu Arg Gly Met Ser Thr His Gly Leu Gln Trp Phe Pro Glu Ile Leu
    50                  55                  60

Asn Asp Asn Ala Tyr Lys Ala Leu Ala Asn Asp Trp Glu Ser Asn Met
65                  70                  75                  80

Ile Arg Leu Ala Met Tyr Val Gly Glu Asn Gly Tyr Ala Ser Asn Pro
                85                  90                  95

Glu Leu Ile Lys Ser Arg Val Ile Lys Gly Ile Asp Leu Ala Ile Glu
            100                 105                 110

Asn Asp Met Tyr Val Ile Val Asp Trp His Val His Ala Pro Gly Asp
            115                 120                 125

Pro Arg Asp Pro Val Tyr Ala Gly Ala Glu Asp Phe Phe Arg Asp Ile
130                 135                 140

Ala Ala Leu Tyr Pro Asn Asn Pro His Ile Ile Tyr Glu Leu Ala Asn
145                 150                 155                 160

Glu Pro Ser Ser Asn Asn Asn Gly Gly Ala Gly Ile Pro Asn Asn Glu
                165                 170                 175

Glu Gly Trp Asn Ala Val Lys Glu Tyr Ala Asp Pro Ile Val Glu Met
            180                 185                 190

Leu Arg Asp Ser Gly Asn Ala Asp Asp Asn Ile Ile Ile Val Gly Ser
        195                 200                 205

Pro Asn Trp Ser Gln Arg Pro Asp Leu Ala Ala Asp Asn Pro Ile Asn
    210                 215                 220

Asp His His Thr Met Tyr Thr Val His Phe Tyr Thr Gly Ser His Ala
225                 230                 235                 240

Ala Ser Thr Glu Ser Tyr Pro Pro Glu Thr Pro Asn Ser Glu Arg Gly
                245                 250                 255

Asn Val Met Ser Asn Thr Arg Tyr Ala Leu Glu Asn Gly Val Ala Val
            260                 265                 270

Phe Ala Thr Glu Trp Gly Thr Ser Gln Ala Asn Gly Asp Gly Gly Pro
        275                 280                 285

Tyr Phe Asp Glu Ala Asp Val Trp Ile Glu Phe Leu Asn Glu Asn Asn
    290                 295                 300

Ile Ser Trp Ala Asn Trp Ser Leu Thr Asn Lys Asn Glu Val Ser Gly
305                 310                 315                 320

Ala Phe Thr Pro Phe Glu Leu Gly Lys Ser Asn Ala Thr Asn Leu Asp
                325                 330                 335

Pro Gly Pro Asp His Val Trp Ala Pro Glu Glu Leu Ser Leu Ser Gly
            340                 345                 350

Glu Tyr Val Arg Ala Arg Ile Lys Gly Val Asn Tyr Glu Pro Ile Asp
        355                 360                 365

Arg Thr Lys Tyr Thr Lys Val Leu Trp Asp Phe Asn Asp Gly Thr Lys
    370                 375                 380

Gln Gly Phe Gly Val Asn Ser Asp Ser Pro Asn Lys Glu Leu Ile Ala
```

```
            385                 390                 395                 400
Val Asp Asn Glu Asn Asn Thr Leu Lys Val Ser Gly Leu Asp Val Ser
                405                 410                 415

Asn Asp Val Ser Asp Gly Asn Phe Trp Ala Asn Ala Arg Leu Ser Ala
                420                 425                 430

Asp Gly Trp Gly Lys Ser Val Asp Ile Leu Gly Ala Glu Lys Leu Thr
            435                 440                 445

Met Asp Val Ile Val Asp Glu Pro Thr Thr Val Ala Ile Ala Ala Ile
        450                 455                 460

Pro Gln Ser Ser Lys Ser Gly Trp Ala Asn Pro Glu Arg Ala Val Arg
465                 470                 475                 480

Val Asn Ala Glu Asp Phe Val Gln Gln Thr Asp Gly Lys Tyr Lys Ala
                485                 490                 495

Gly Leu Thr Ile Thr Gly Glu Asp Ala Pro Asn Leu Lys Asn Ile Ala
            500                 505                 510

Phe His Glu Glu Asp Asn Asn Met Asn Asn Ile Ile Leu Phe Val Gly
        515                 520                 525

Thr Asp Ala Ala Asp Val Ile Tyr Leu Asp Asn Ile Lys Val Ile Gly
    530                 535                 540

Thr Glu Val Glu Ile Pro Val Val His Asp Pro Lys Gly Glu Ala Val
545                 550                 555                 560

Leu Pro Ser Val Phe Glu Asp Gly Thr Arg Gln Gly Trp Asp Trp Ala
                565                 570                 575

Gly Glu Ser Gly Val Lys Thr Ala Leu Thr Ile Glu Glu Ala Asn Gly
            580                 585                 590

Ser Asn Ala Leu Ser Trp Glu Phe Gly Tyr Pro Glu Val Lys Pro Ser
        595                 600                 605

Asp Asn Trp Ala Thr Ala Pro Arg Leu Asp Phe Trp Lys Ser Asp Leu
    610                 615                 620

Val Arg Gly Glu Asn Asp Tyr Val Ala Phe Asp Phe Tyr Leu Asp Pro
625                 630                 635                 640

Val Arg Ala Thr Glu Gly Ala Met Asn Ile Asn Leu Val Phe Gln Pro
                645                 650                 655

Pro Thr Asn Gly Tyr Trp Val Gln Ala Pro Lys Thr Tyr Thr Ile Asn
            660                 665                 670

Phe Asp Glu Leu Glu Glu Ala Asn Gln Val Asn Gly Leu Tyr His Tyr
        675                 680                 685

Glu Val Lys Ile Asn Val Arg Asp Ile Thr Asn Ile Gln Asp Asp Thr
    690                 695                 700

Leu Leu Arg Asn Met Met Ile Ile Phe Ala Asp Val Glu Ser Asp Phe
705                 710                 715                 720

Ala Gly Arg Val Phe Val Asp Asn Val Arg Phe Glu Gly Ala Ala Thr
                725                 730                 735

Thr Glu Pro Val Glu Pro Glu Pro Val Asp Pro Gly Glu Glu Thr Pro
            740                 745                 750

Pro Val Asp Glu Lys Glu Ala Lys Lys Glu Gln Lys Glu Ala Glu Lys
        755                 760                 765

Glu Glu Lys Glu Glu
    770

<210> SEQ ID NO 10
<211> LENGTH: 941
<212> TYPE: PRT
<213> ORGANISM: Unknown
<220> FEATURE:
```

<223> OTHER INFORMATION: Bacillus species

<400> SEQUENCE: 10

```
Met Lys Ile Lys Gln Ile Lys Gln Ser Leu Ser Leu Leu Leu Ile
1               5                   10                  15

Thr Leu Ile Met Ser Leu Phe Val Pro Met Ala Ser Ala Asn Thr Asn
            20                  25                  30

Glu Ser Lys Ser Asn Ala Phe Pro Phe Ser Asp Val Lys Lys Thr Ser
        35                  40                  45

Trp Ser Phe Pro Tyr Ile Lys Asp Leu Tyr Glu Gln Glu Val Ile Thr
    50                  55                  60

Gly Thr Ser Ala Thr Thr Phe Ser Pro Thr Asp Ser Val Thr Arg Ala
65                  70                  75                  80

Gln Phe Thr Val Met Leu Thr Arg Gly Leu Gly Leu Glu Ala Ser Ser
                85                  90                  95

Lys Asp Tyr Pro Phe Lys Asp Arg Lys Asn Trp Ala Tyr Lys Glu Ile
            100                 105                 110

Gln Ala Ala Tyr Glu Ala Gly Ile Val Thr Gly Lys Thr Asn Gly Glu
        115                 120                 125

Phe Ala Pro Asn Glu Asn Ile Thr Arg Glu Gln Met Ala Ala Met Ala
130                 135                 140

Val Arg Ala Tyr Glu Tyr Leu Glu Asn Glu Leu Ser Leu Pro Glu Glu
145                 150                 155                 160

Gln Arg Glu Tyr Asn Asp Ser Ser Ile Ser Thr Phe Ala Gln Asp
                165                 170                 175

Ala Val Gln Lys Ala Tyr Val Leu Glu Leu Met Glu Gly Asn Thr Asp
            180                 185                 190

Gly Tyr Phe Gln Pro Lys Arg Asn Ser Thr Arg Glu Gln Ser Ala Lys
        195                 200                 205

Val Ile Ser Thr Leu Leu Trp Lys Val Ala Ser His Asp Tyr Leu Tyr
    210                 215                 220

His Thr Glu Ala Val Lys Ser Pro Ser Glu Ala Gly Ala Leu Gln Leu
225                 230                 235                 240

Val Glu Leu Asn Gly Gln Leu Thr Leu Ala Gly Glu Asp Gly Thr Pro
                245                 250                 255

Val Gln Leu Arg Gly Met Ser Thr His Gly Leu Gln Trp Phe Gly Glu
            260                 265                 270

Ile Val Asn Glu Asn Ala Phe Val Ala Leu Ser Asn Asp Trp Gly Ser
        275                 280                 285

Asn Met Ile Arg Leu Ala Met Tyr Ile Gly Glu Asn Gly Tyr Ala Thr
    290                 295                 300

Asn Pro Glu Val Lys Asp Leu Val Tyr Glu Gly Ile Glu Leu Ala Phe
305                 310                 315                 320

Glu His Asp Met Tyr Val Ile Val Asp Trp His Val His Ala Pro Gly
                325                 330                 335

Asp Pro Arg Ala Asp Val Tyr Ser Gly Ala Tyr Asp Phe Phe Glu Glu
            340                 345                 350

Ile Ala Asp His Tyr Lys Asp His Pro Lys Asn His Tyr Ile Ile Trp
        355                 360                 365

Glu Leu Ala Asn Glu Pro Ser Pro Asn Asn Gly Gly Pro Gly Leu
    370                 375                 380

Thr Asn Asp Glu Lys Gly Trp Glu Ala Val Lys Glu Tyr Ala Glu Pro
385                 390                 395                 400

Ile Val Glu Met Leu Arg Glu Lys Gly Asp Asn Met Ile Leu Val Gly
```

```
            405                 410                 415
Asn Pro Asn Trp Ser Gln Arg Pro Asp Leu Ser Ala Asp Asn Pro Ile
            420                 425                 430

Asp Ala Glu Asn Ile Met Tyr Ser Val His Phe Tyr Thr Gly Ser His
            435                 440                 445

Gly Ala Ser His Ile Gly Tyr Pro Glu Gly Thr Pro Ser Ser Glu Arg
            450                 455                 460

Ser Asn Val Met Ala Asn Val Arg Tyr Ala Leu Asp Asn Gly Val Ala
465                 470                 475                 480

Val Phe Ala Thr Glu Trp Gly Thr Ser Gln Ala Asn Gly Asp Gly Gly
            485                 490                 495

Pro Tyr Phe Asp Glu Ala Asp Val Trp Leu Asn Phe Leu Asn Lys His
            500                 505                 510

Asn Ile Ser Trp Ala Asn Trp Ser Leu Thr Asn Lys Asn Glu Ile Ser
            515                 520                 525

Gly Ala Phe Thr Pro Phe Glu Leu Gly Arg Thr Asp Ala Thr Asp Leu
            530                 535                 540

Asp Pro Gly Ala Asn Gln Val Trp Ala Pro Glu Leu Ser Leu Ser
545                 550                 555                 560

Gly Glu Tyr Val Arg Ala Arg Ile Lys Gly Ile Glu Tyr Thr Pro Ile
            565                 570                 575

Asp Arg Thr Lys Phe Thr Lys Leu Val Trp Asp Phe Asn Asp Gly Thr
            580                 585                 590

Thr Gln Gly Phe Gln Val Asn Gly Asp Ser Pro Asn Lys Glu Ser Ile
            595                 600                 605

Thr Leu Ser Asn Asn Asp Ala Leu Gln Ile Glu Gly Leu Asn Val
            610                 615                 620

Ser Asn Asp Ile Ser Glu Gly Asn Tyr Trp Asp Asn Val Arg Leu Ser
625                 630                 635                 640

Ala Asp Gly Trp Ser Glu Asn Val Asp Ile Leu Gly Ala Thr Glu Leu
            645                 650                 655

Thr Ile Asp Val Ile Val Glu Glu Pro Thr Thr Val Ser Ile Ala Ala
            660                 665                 670

Ile Pro Gln Gly Pro Ala Ala Gly Trp Ala Asn Pro Thr Arg Ala Ile
            675                 680                 685

Lys Val Thr Glu Asp Asp Phe Glu Ser Phe Gly Asp Gly Tyr Lys Ala
            690                 695                 700

Leu Val Thr Ile Thr Ser Glu Asp Ser Pro Ser Leu Glu Thr Ile Ala
705                 710                 715                 720

Thr Ser Pro Glu Asp Asn Thr Met Ser Asn Ile Ile Leu Phe Val Gly
            725                 730                 735

Thr Glu Asp Ala Asp Val Ile Ser Leu Asp Asn Ile Thr Val Ser Gly
            740                 745                 750

Thr Glu Ile Glu Ile Glu Val Ile His Asp Glu Lys Gly Thr Ala Thr
            755                 760                 765

Leu Pro Ser Thr Phe Glu Asp Gly Thr Arg Gln Gly Trp Asp Trp His
770                 775                 780

Thr Glu Ser Gly Val Lys Thr Ala Leu Thr Ile Glu Glu Ala Asn Gly
785                 790                 795                 800

Ser Asn Ala Leu Ser Trp Glu Tyr Ala Tyr Pro Glu Val Lys Pro Ser
            805                 810                 815

Asp Gly Trp Ala Thr Ala Pro Arg Leu Asp Phe Trp Lys Asp Glu Leu
            820                 825                 830
```

-continued

| | | | | | | | | | | | | |
|---|---|---|---|---|---|---|---|---|---|---|---|---|
| Val | Arg | Gly 835 | Thr | Ser | Asp | Tyr | Ile 840 | Ser | Phe | Asp | Phe 845 | Tyr | Ile | Asp | Ala |
| Val | Arg 850 | Ala | Ser | Glu | Gly | Ala 855 | Ile | Ser | Ile | Asn 860 | Ala | Val | Phe | Gln | Pro |
| Pro 865 | Ala | Asn | Gly | Tyr | Trp 870 | Gln | Glu | Val | Pro | Thr 875 | Thr | Phe | Glu | Ile | Asp 880 |
| Leu | Thr | Glu | Leu | Asp 885 | Ser | Ala | Thr | Val | Thr 890 | Ser | Asp | Glu | Leu | Tyr 895 | His |
| Tyr | Glu | Val | Lys 900 | Ile | Asn | Ile | Arg | Asp 905 | Ile | Glu | Ala | Ile | Thr 910 | Asp | Asp |
| Thr | Glu | Leu 915 | Arg | Asn | Leu | Leu | Leu 920 | Ile | Phe | Ala | Asp | Glu 925 | Asp | Ser | Asp |
| Phe | Ala | Gly 930 | Arg | Val | Phe | Val 935 | Asp | Asn | Val | Arg | Phe 940 | Glu |